(12) United States Patent
Morris et al.

(10) Patent No.: US 12,193,714 B2
(45) Date of Patent: Jan. 14, 2025

(54) CONNECTORS, SYSTEMS, AND METHODS THEREOF

(71) Applicant: GLOBUS MEDICAL, INC., Audubon, PA (US)

(72) Inventors: Ross Morris, Norristown, PA (US); Patrick Murray, Collegeville, PA (US)

(73) Assignee: Globus Medical Inc., Audubon, PA (US)

( * ) Notice: Subject to any disclaimer, the term of this patent is extended or adjusted under 35 U.S.C. 154(b) by 420 days.

(21) Appl. No.: 17/314,104

(22) Filed: May 7, 2021

(65) Prior Publication Data
US 2022/0354546 A1     Nov. 10, 2022

(51) Int. Cl.
*A61B 17/70*     (2006.01)
(52) U.S. Cl.
CPC ........ *A61B 17/7052* (2013.01); *A61B 17/705* (2013.01)

(58) Field of Classification Search
CPC ......... A61B 17/7049–17/7052; A61B 17/7043
See application file for complete search history.

(56) References Cited

U.S. PATENT DOCUMENTS

| | | | |
|---|---|---|---|
| 10,624,679 B2* | 4/2020 | Murray | A61B 17/705 |
| 2011/0218578 A1* | 9/2011 | Jackson | A61B 17/702 606/305 |
| 2015/0119941 A1* | 4/2015 | Daniels | A61B 17/7056 606/276 |
| 2017/0281237 A1* | 10/2017 | Murray | A61B 17/7004 |
| 2021/0030448 A1* | 2/2021 | Yoder | A61B 17/7041 |
| 2021/0298793 A1* | 9/2021 | Schwiesau | A61B 17/7049 |

* cited by examiner

*Primary Examiner* — Julianna N Harvey

(57) ABSTRACT

Implants, systems, and methods for connecting one or more spinal rods. The spinal connector implants may be used in revision surgeries to extend fixation to adjacent level(s). The implants may be configured for parallel, perpendicular, or in-line connection of adjacent rods or may be secured to a screw head of an existing screw.

19 Claims, 34 Drawing Sheets

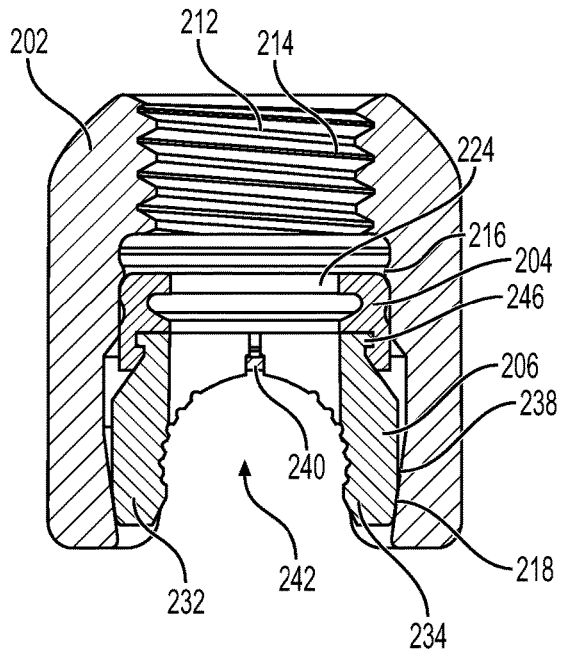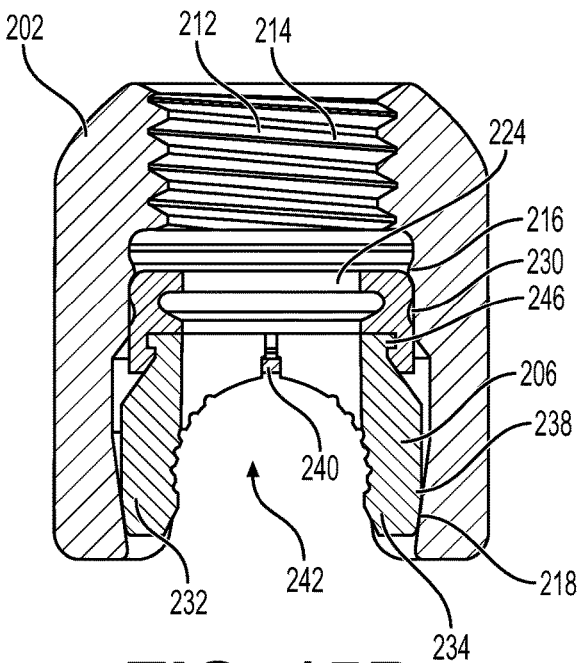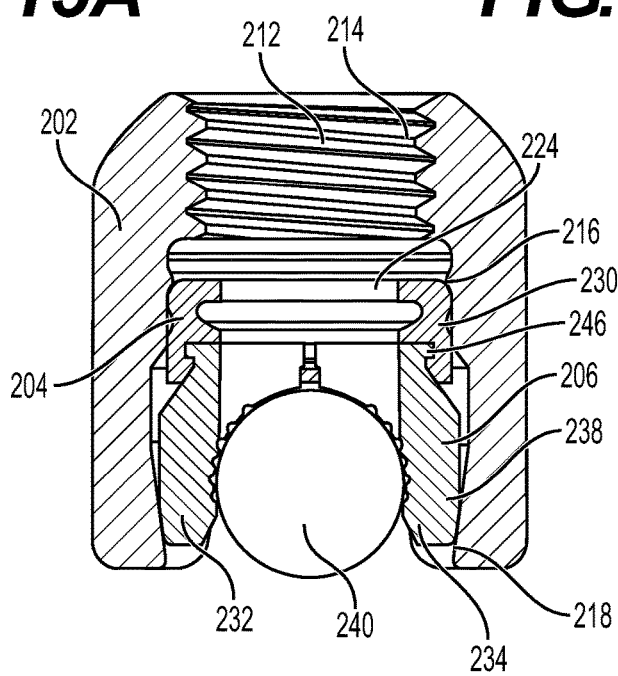
FIG. 15A
FIG. 15B
FIG. 15C

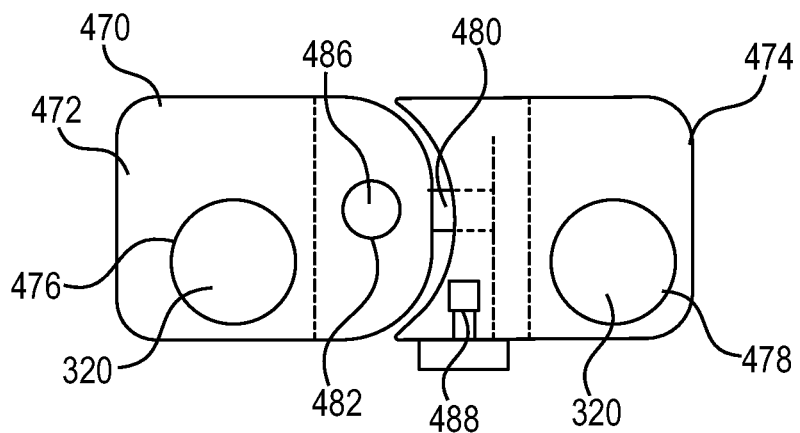
FIG. 29A
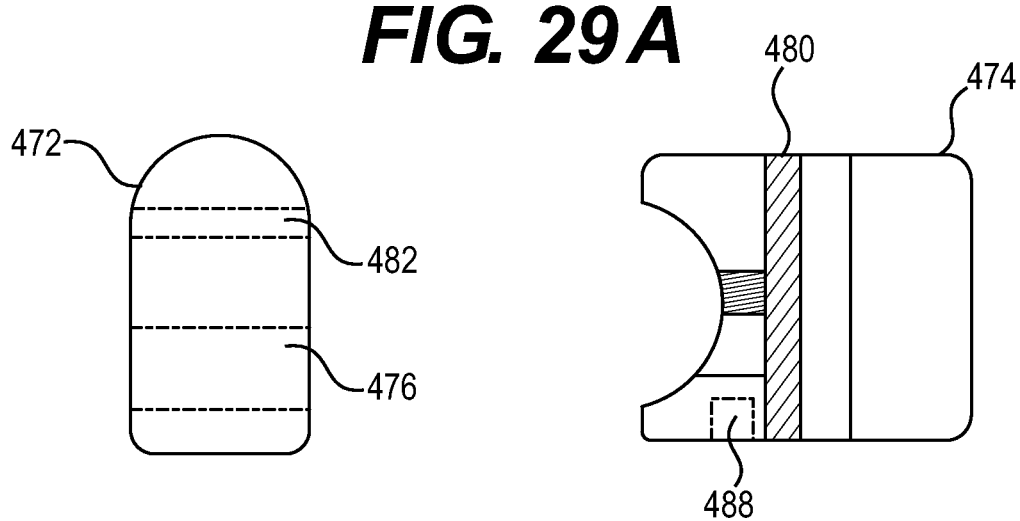
FIG. 29B  FIG. 29C
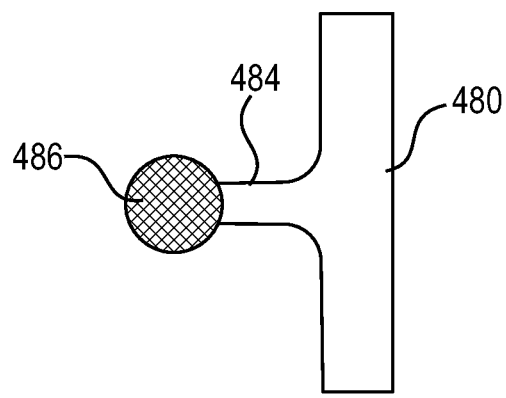
FIG. 29D

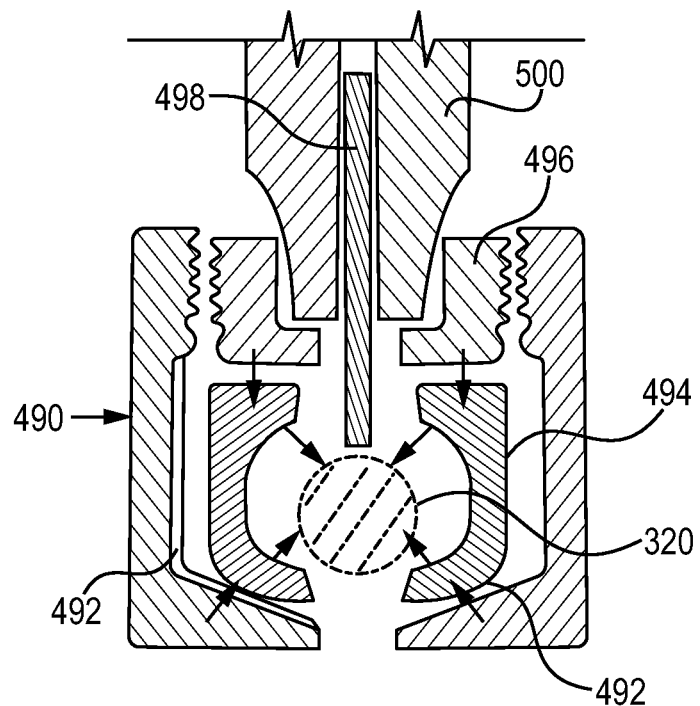
FIG. 30
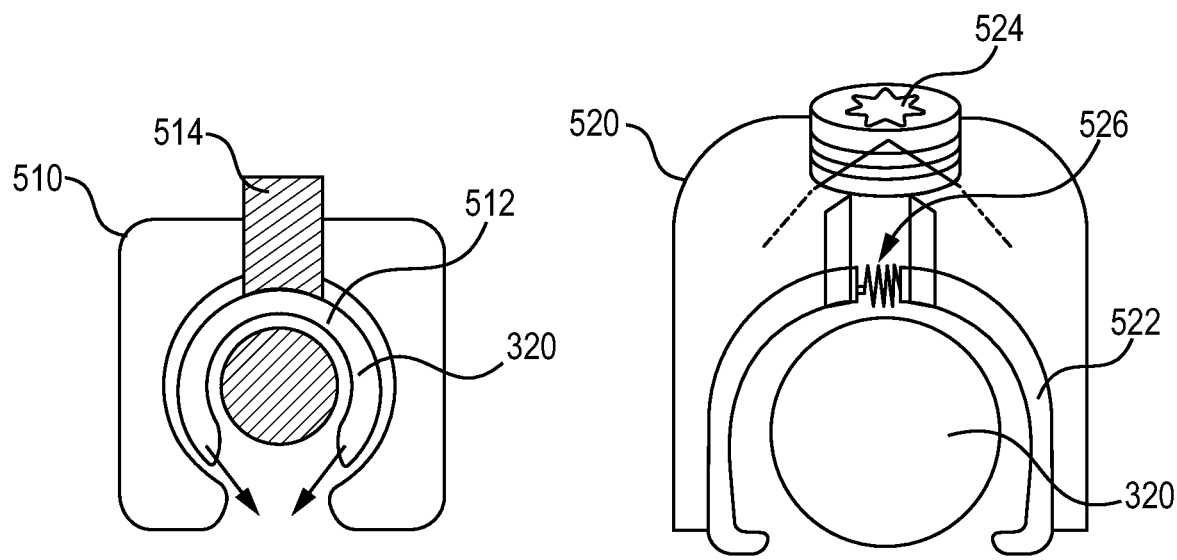
FIG. 31  FIG. 32

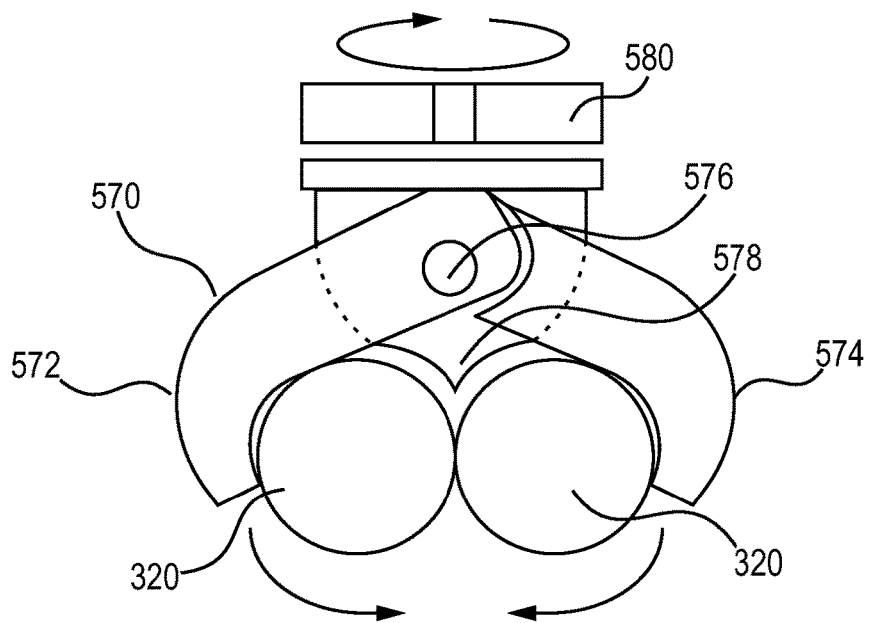
FIG. 36
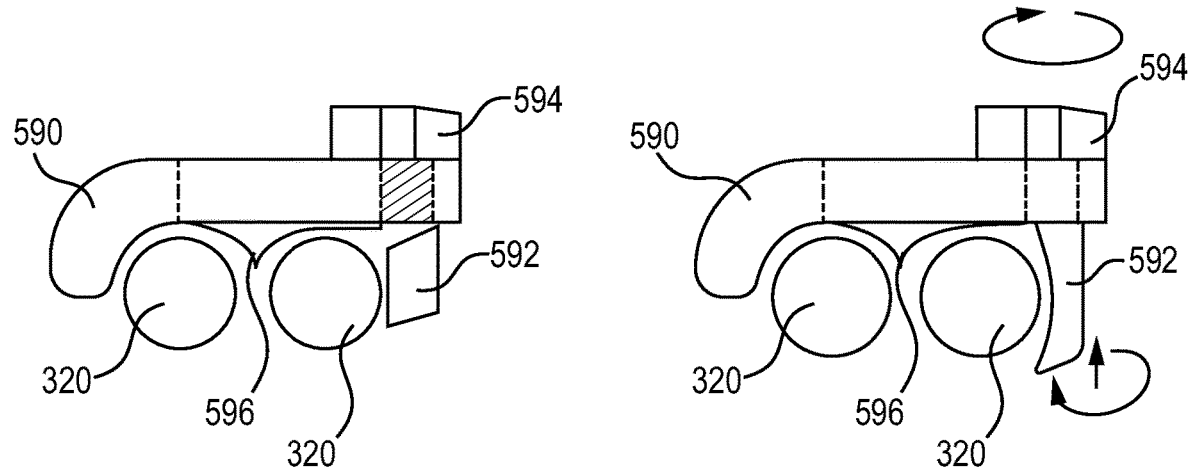
FIG. 37A  FIG. 37B

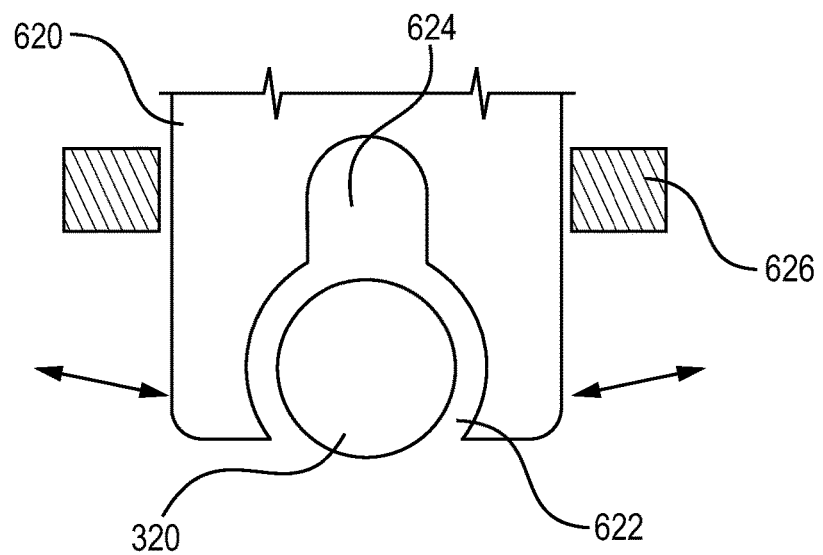
FIG. 40
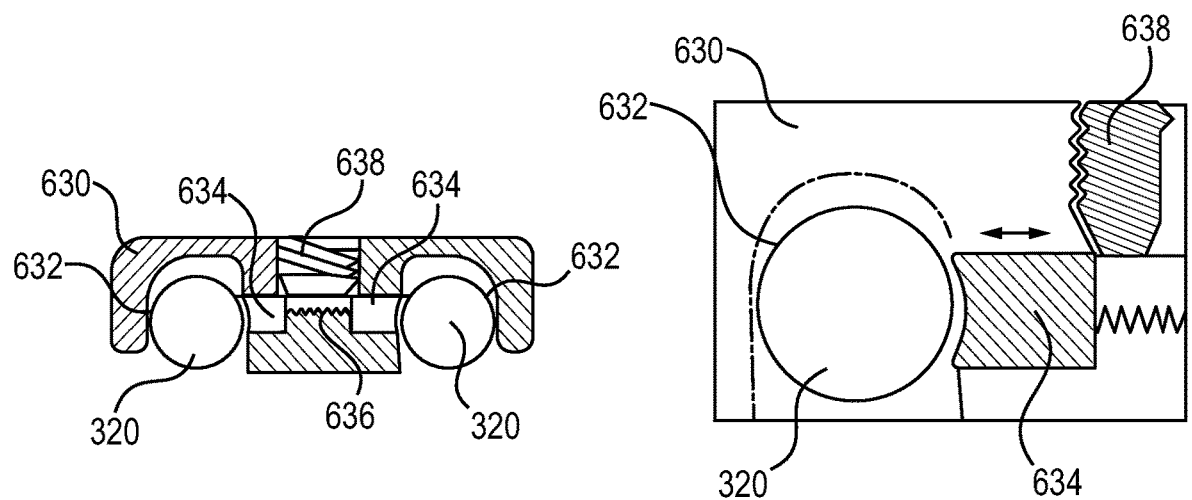
FIG. 41A  FIG. 41B

CONNECTORS, SYSTEMS, AND METHODS THEREOF

FIELD OF THE INVENTION

The present application relates generally to connectors, and more particularly, to rod connector implants for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine.

At times, spinal surgeons may be required to add additional fixation to spinal segments adjacent to previously instrumented spinal segments or levels. In these cases, the hardware from the initial or primary surgery may interfere with placement of new fixation for the adjacent level or levels. Therefore, there is a need for connector implants which attach to the existing spinal fusion construct along or on one end and extend fixation to adjacent levels in need of fusion.

In other situations, screw constructs in the cervical spine may be too close together to allow fitting a traditional rod clamping connector between two screw heads. In some cases, it may be useful to have connectors which attach to an existing screw. There exists a need for improved spinal connector implants that can be used in primary and revision surgeries to extend fixation to adjacent levels.

SUMMARY OF THE INVENTION

To meet this and other needs, devices, systems, and methods of attaching a connector to a rod or screw and extending fixation to adjacent level(s) are provided. The connector implants may be used during a primary surgery or during a revision surgery. The connector implants may be configured to secure two rods, such as parallel, perpendicular rods, in-line, or angled rods. The connectors may be static or may have pivoting or rotating components. The connectors may offer surgeons the ability to attach instrumentation to existing cervical and/or thoracolumbar spine screw constructs as patient anatomy allows. Attaching directly to existing constructs may save operating time, cause less disruption to the patient, and may minimize patient recovery time.

According to one embodiment, a connector implant includes a connector having a body with an upper surface, a lower surface, a front, a back, and two opposed side surfaces. The connector has a first clamping portion and a second clamping portion. The first clamping portion defines a first passage sized and dimensioned to receive a first rod, and the second clamping portion defines a second passage sized and dimensioned to receive a second rod. The connector has an engagement recess defined with the side surface. The engagement recess may be a T-shaped indentation configured to interface with an implant inserter to help orient and manipulate the connector into position. The connector implant may also include first and second locking members configured to secure the first and second rods in the connector.

The connector implant may include one or more of the following features. The connector may include two opposed engagement recesses defined within the side surfaces near the upper surface of the implant. The T-shaped indentation(s) may include a first recessed portion extending along the side surface from the front to the back of the connector. The T-shaped indentation(s) may include a second recessed portion extending from the middle of the first recessed portion downward towards the lower surface of the connector. The first recessed portion may include a horizontal bar having a length greater than its width. The second recessed portion may include a vertical bar having a length greater than its width. The T-shaped indentation may be positioned at a mid-line between the first and second clamping portions. The first and second passages may be aligned in parallel. The first and/or second passage may have a dual diameter to allow for the respective first or second rod to be captured in three-point contact.

According to another embodiment, an implant assembly includes an implant housing including a first portion defining a first rod slot configured for securing a first spinal rod and a second portion configured for attaching a second spinal rod to a bone fastener. The second portion of the housing includes a pair of opposed tabs extending downwardly. The tabs are configured to engage a second rod slot in a head of the bone fastener. A posted locking cap having a threaded portion is receivable through a hole in the second portion of the implant housing and configured to contact the second spinal rod. The threaded portion is configured to mate with internal threads in the head of the bone fastener to secure the second spinal rod therein. A locking nut defines internal threads configured to mate with the posted locking cap, thereby securing the implant housing to the bone fastener.

The implant assembly may include one or more of the following features. The posted locking cap may be dual-threaded with two distinct threaded portions: an upper portion to engage the locking nut and a lower portion to engage the internal threads in the head of the bone fastener. A bottom surface of the locking nut may contact an upper surface of the implant housing to secure implant housing to the bone fastener. The locking nut may have teeth or a roughened surface cut into the bottom surface to prevent loosening. The first portion of the implant housing may be a tulip head with two opposing sides spaced apart by the first rod slot. The opposing sides of the tulip head may define internal threads configured to mate with exterior threads on a locking member. The first rod slot may have a dual diameter in a bottom of the first rod slot, thereby allowing the first spinal rod to be captured in three point contact.

According to another embodiment, a connector assembly includes a connector body having a first clamping portion and a second clamping portion. The first clamping portion may have a first passage sized and dimensioned to receive a first rod, and the second clamping portion may have a second passage sized and dimensioned to receive a second rod. The first clamping portion defines an opening extending therethrough in fluid communication with the first rod slot. An upper portion of the opening includes a threaded portion, a lower portion of the opening defines a tapered inner surface, and a modular bump is located between the threaded portion and the tapered inner surface. A locking assembly includes a clamp engaged with a saddle positioned within the opening. The clamp includes a first clamp portion and a second clamp portion separated by a slit. A portion of an outer surface of the first and second clamp portions includes a tapered outer surface configured to abut and engage the tapered inner surface of the connector body. When the saddle and clamp translate downward, the clamp locks around the first rod.

The connector assembly may include one or more of the following features. The saddle may include a ring-like body with a bore extending therethrough. An annular groove defined within the bore may secure a ledge at the top of the clamp to the saddle. The groove in the saddle may be elliptical in shape and the ledge of the clamp may have a mating elliptical shape. When the saddle is above the modular bump, the clamp is configured to expand to accept or release the first spinal rod, and when the saddle is below the modular bump, the clamp is locked around the first spinal rod.

According to yet further embodiments, examples of connectors are shown for connecting rods of varying diameters. The connectors may be configured to pivot or rotate to align the spinal rods as desired. The spinal rods may be connected in parallel, perpendicular, in-line, or angled with respect to one another.

Also provided are kits including implants of varying types and sizes, rods, instruments, and other components for performing a spinal fusion.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 15A-15C show cross-sections of the top loading connector portion, with the saddle and clamp, and engaging a spinal rod in a downward captured position;

FIGS. 29A-29D show a pivoting connector with a cammed T-jack according to one embodiment;

FIG. 30 shows a connector housing configured to accept a range of rod diameters according to one embodiment;

FIG. 31 shows a connector housing with a fork clamp to secure the rod according to one embodiment;

FIG. 32 shows a connector housing with a prong clamp to secure the rod according to one embodiment;

FIG. 36 shows a clamping connector according to one embodiment;

FIGS. 37A-37B show a parallel connector with a rotating cam according to one embodiment;

FIG. 40 shows a top loading connector portion according to one embodiment; and

FIGS. 41A-41B show a parallel connector with sliding blockers according to one embodiment.

DETAILED DESCRIPTION OF THE INVENTION

Figure 1A:
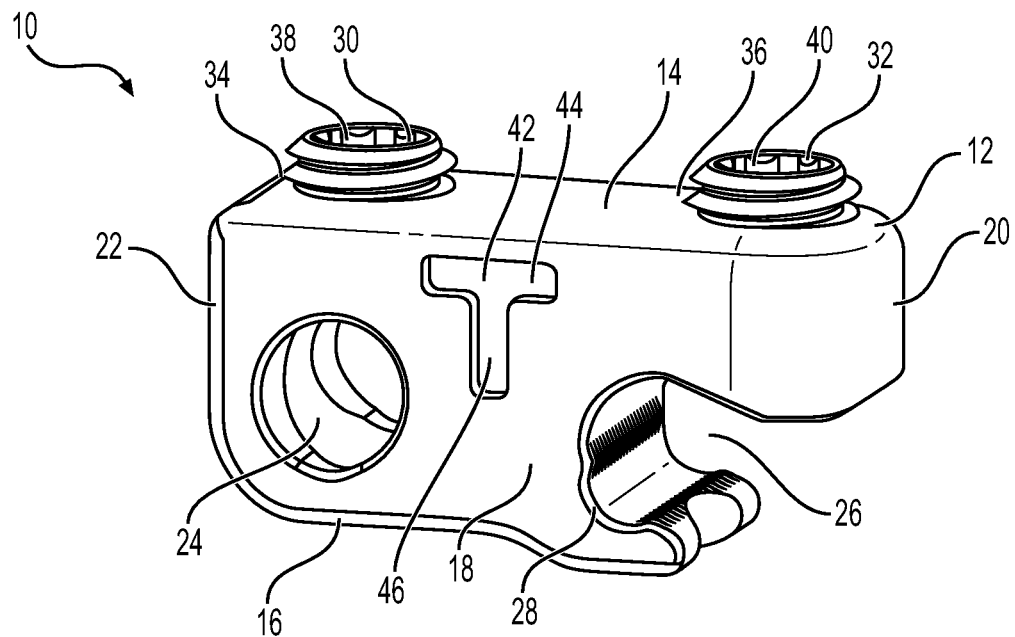
FIGS. 1A-1B show perspective and cross-sectional views, respectively, of a parallel connector with a closed portion and an open portion for securing two parallel rods according to one embodiment.

Embodiments of the disclosure are generally directed to implants, systems, and methods for attaching a connector to one or more rods or screws. Specifically, embodiments are directed to implants and systems configured to add additional fixation, for example, to spinal segments adjacent to previously instrumented levels. Although described generally with reference to the spine, it will be appreciated that the implants and systems described herein may be applied to other orthopedic locations and applications, such as trauma.

The present disclosure relates to components, systems, and methods for connecting one device to another device. For example, one elongate implant, such as a first rod, may be coupled to another elongate implant, such as a second rod. The elongate implants, such as rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a scoliosis operation, or at a later surgery, for example, in a revision surgery. In a revision surgery, connectors may be used to connect new fixation constructs to existing fixation constructs without the need to remove the original hardware.

Connectors may be used to connect instrumentation of different sizes used in different areas of the spine or connectors may be used to connect new fixation constructs to existing fixation constructs without the need to remove index surgery hardware. A benefit to such direct attachment to existing constructs saves operating time, causes less disruption to the patient, and minimizes patient healing time. The ability of the connectors to maintain connection with existing constructs can maximize utility in cases of varying patient anatomy and existing spinal constructs. The different connection modes provided in the following exemplary embodiments offer a range of options to be chosen based on a specific clinical scenario and/or surgeon preference. Thus, although certain configurations are shown herein, it is envisioned that any suitable number, type, and selection of connectors, implants, rods, and the like may be chosen and configured by a skilled surgeon.

In some cases, existing bone growth around previously instrumented spinal segments may make attachment to the previously placed spinal rod challenging. A portion of this bone growth may need to be cleared away in order to connect the new instrumentation to the previously placed spinal rods. However, this bone growth may be important for stabilizing the spine and maintaining relief of patient symptoms. Therefore, it may be advantageous to provide connectors which minimize the amount of area needed around the rod for attachment so that less bone growth needs to be removed during the revision surgery. Additionally, removing bone from the top of previous instrumentation may be less difficult than removing bone from the sides or underneath of previous instrumentation. In some embodiments, the spinal connector implants may be used in revision surgeries to extend fixation to adjacent level(s), which minimizes contact on the rod and can be connected to the previous instrumentation from above in a top loading manner, side-loaded from the side, or loaded from the bottom.

The connectors and other components described herein may be manufactured from any suitable biocompatible materials including, but not limited to, metals such as, titanium, stainless steel, titanium alloys, non-titanium metallic alloys; polymeric materials, such as plastics, plastic composites, poly ether ether ketone (PEEK); ceramics, and other biocompatible materials.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

Figure 1B:
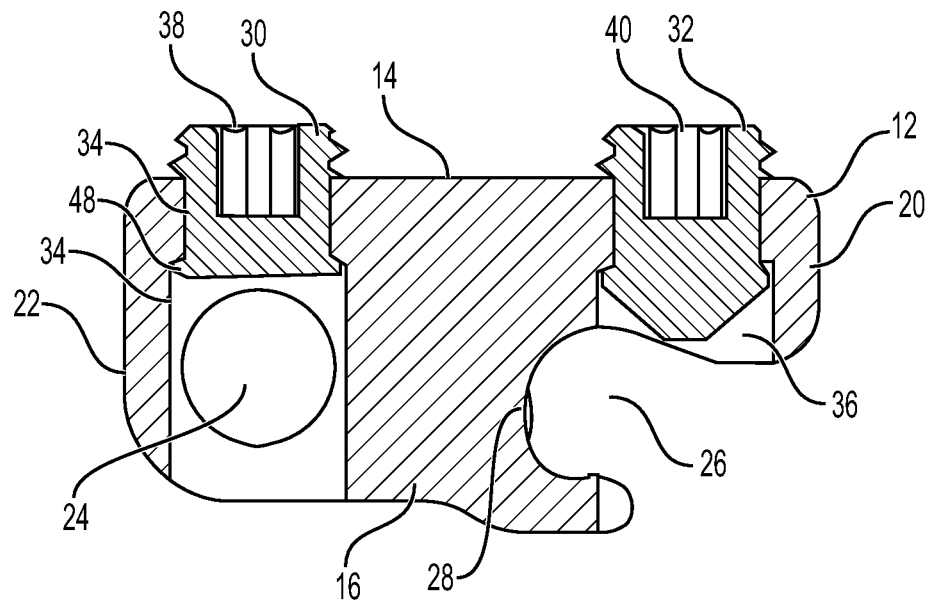

Referring now to FIGS. 1A-1B, a parallel connector or implant 10 is shown according to one embodiment. The implant 10 may include a closed portion and an open portion for receiving two parallel elongate members or rods. For example, the implant 10 may engage with a first elongate member or first spinal rod and a second elongate member or second spinal rod to provide additional fixation during a primary surgery or a revision surgery.

The implant 10 has a main body 12 including an upper surface 14, a lower surface 16, opposed side surfaces 18, a nose or front surface 20, and a back or rear surface 22. For example, the upper surface 14, side surfaces 18, and rear surface 22 may be generally flat or planar and the front surface 20 may be generally rounded or convex. The main body 12 defines a first opening, recess, or rod slot 24 sized and dimensioned to accept a first spinal rod and a second opening, recess, or rod slot 26 sized and dimensioned to accept a second spinal rod.

In this embodiment, the first rod slot 24 may be a closed slot 24 for fully encircling the first spinal rod. The closed slot 24 may extend between the side surfaces 18 of the main body 12. The rod may be radially enclosed by the connector 10 for maximum strength. The rod may be captured in the closed slot 24 in three-point contact due to a dual diameter of the bottom of the rod slot 24. The second rod slot 26 may be an open slot 26 recessed into the front surface 20 of the implant 10. The open slot 26 may define a generally c-shaped recess sized and dimensioned to receive the rod when side-loaded therein. The open slot 26 may optionally include a roughened surface or a plurality of grooves 28 cut into the connector 10 for added grip onto the rod.

The implant 10 includes a first set screw or first locking member 30 configured to secure the first rod in the first rod slot 24. The main body 12 has a first hole 34 in fluid communication with the first rod slot 24. The first hole 34 may be generally perpendicular to the first rod slot 24. The first hole 34 may include a threaded portion around an inner periphery of the hole 34. The first locking member 30 is positionable within the first hole 34 and is able to travel up and down within the threaded hole 34. When in a downward position, a bottom surface of the locking member 30 is configured to contact and secure the spinal rod within the first rod slot 24 in the main body 12 of the implant 10.

As best seen in FIG. 1B, the bottom surface of the locking member 38 may be generally planar or flat and may have a flange 48 or enlarged outer diameter in relation to the body of the locking member 30. The flange 48 may help to keep the locking member 30 assembled to the connector body 12. The first locking member 30 may include a threaded portion around an outer surface, which is configured to threadedly mate with the first hole 34. The first locking member 30 may define an instrument recess 38 in an upper surface of the first locking member 30. The instrument recess 38 is configured to be engaged by an instrument, such as a driver, for rotating the locking member 30 into the locked position. The connector 10 may be pre-loaded with the locking sett screw 30 prior to surgery.

The implant 10 includes a second set screw or a second locking member 32 configured to secure the second rod in the second rod slot 26. The main body 12 has a second hole 36 in fluid communication with the second rod slot 26. The hole axis of the second hole 36 may be generally parallel to the hole axis of the first hole 34. It will be appreciated that the second hole 36 may also be angled or otherwise configured to intersect with the second rod slot 26. The second hole 36 may include a threaded portion around an inner periphery of the hole 36. The second locking member 32 is positionable within the second hole 36 and is able to travel up and down within the threaded hole 36. When in a downward position, a bottom surface of the locking member 32 is configured to contact and secure the spinal rod within the second rod slot 26 in the main body 12 of the implant 10. Once the rod is in place, the set screw 32 may capture the rod into three point contact due to the dual diameter at the back of the rod slot 26.

The bottom surface of the second locking member 32 may be angled or pointed to form a conical bottom to secure the rod. The second locking member 32 may include a threaded portion around an outer surface, which is configured to threadedly mate with the second hole 36. The second locking member 32 may define an instrument recess 40 in an upper surface of the second locking member 32 configured to be engaged by an instrument, such as a driver, for rotating the locking member 32 into the locked position. The connector 10 may be pre-loaded with the locking set screw 32 prior to surgery.

As shown in FIG. 1A, the main body 12 of the implant 10 may include one or more engagement recesses 42 for engagement with an insertion instrument. For example, two opposed engagement recesses 42 may be defined within the side surfaces 18, near the top 14 of the implant 10. The engagement recess 42 may include a T-shaped indentation. The recess 42 may include a first recessed portion 44 extending along the side surface 18 from the front 20 to the back 22 of the implant 10 and a second recessed portion 46 extending from the middle of the first recessed portion 44 downward towards the bottom surface 16. The first recessed portion 44 may include a horizontal bar or linear groove having a length greater than its width. The second recessed portion 46 may include a vertical bar or linear groove having a length greater than its width. The second recessed portion 46 may have a length greater than the first recessed portion 44. The implant 10 may define corresponding T-shaped recesses 42 on both sides of the connector 10 near the upper mid-line area. The T-shaped recesses 42 may be centrally located at the mid-line between the rod slots 24, 26. The T-shaped engagement recesses 42 may be used with an implant inserter to help orient and manipulate the connector 10 into place in the patient. The open/closed connector 10 may be suitable for two rods in the cervical thoracic spine, for example.

Figure 2:
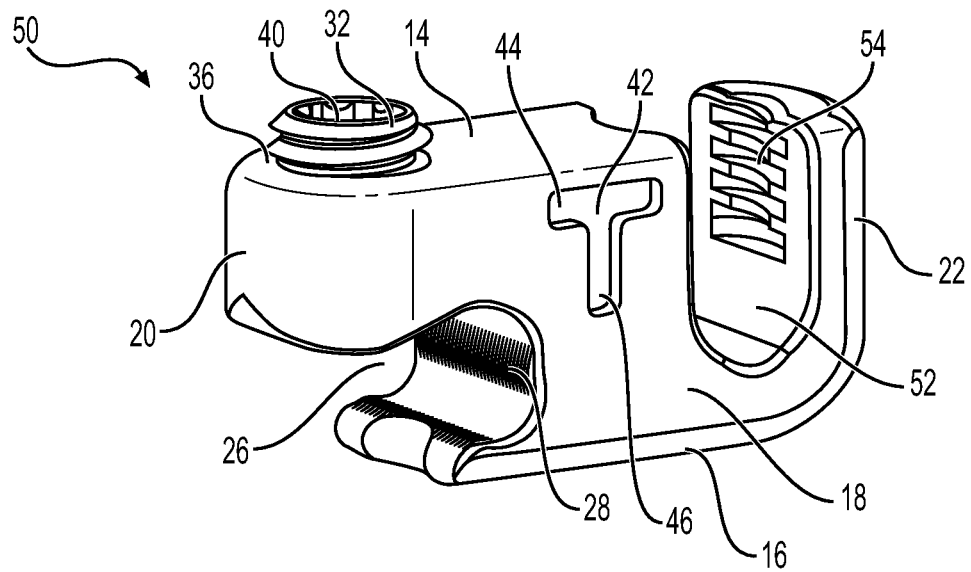
FIG. 2 shows a perspective view of a parallel connector with an open portion and a headed portion for securing two parallel rods according to one embodiment.

Referring now to FIG. 2, a parallel connector or implant 50 is shown according to one embodiment. Similar to implant 10, implant 50 includes an open portion including open rod slot 26 for receiving one rod and the t-shaped engagement recesses 42 for mating with an inserter. Implant 10 also includes a headed portion for receiving the other rod.

The headed portion of the implant 50 may be in the form of a tulip with two opposing sides spaced apart by a rod slot 52 configured to receive the spinal rod. The rod may be top-loaded into the rod slot 52. The opposing sides of the tulip head may define internal threads 54 configured to mate with the exterior threads on a locking member from cervical or thoracic screw systems. The rod may be captured in three point contact due to the dual diameter of the bottom of the rod slot 52. The connecter 50 may or may not contain reduction features for use with instruments that assist in pushing the rod into the rod slot 52 before a locking cap is in place. In some embodiments, the reduction features include dovetails. The open/headed connector 50 may be suitable for two rods in the cervical thoracic spine, for example.

Figure 3:
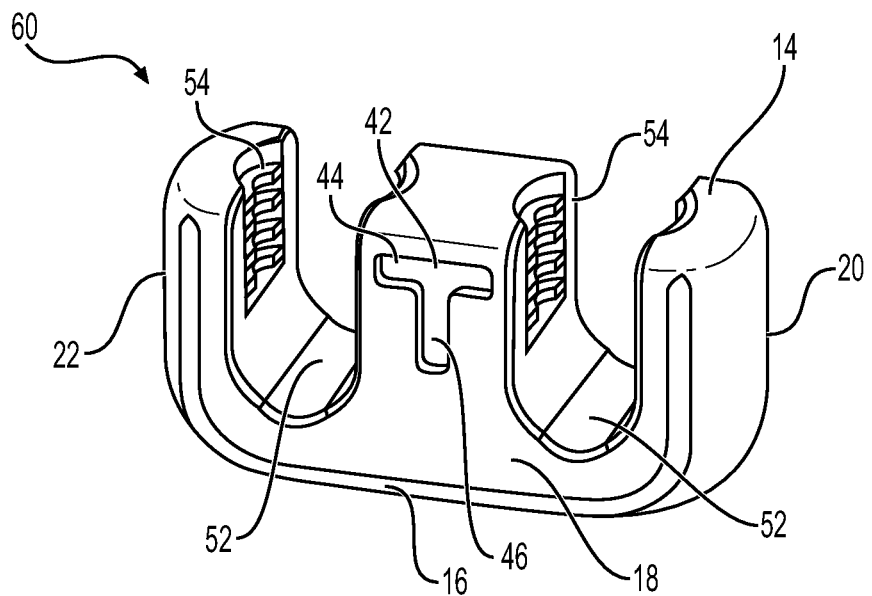
FIG. 3 shows a perspective view of a double headed parallel connector according to one embodiment.

Referring now to FIG. 3, a parallel connector or implant 60 is shown according to one embodiment. Similar to implant 50, implant 60 includes a headed portion including rod slot 52 for receiving one rod and the T-shaped engagement recesses 42 for mating with an inserter. Implant 60 also includes a second headed portion for receiving the other rod.

For double headed implant 60, two identical headed portions with rod slots 52 may be used to receive the rods. When two headed partials are used together in this manner, the rod slots 52 may be parallel or angulated relative to each other (in either cephalad/caudal or medial/lateral directions). The rods may be top-loaded into the rod slots 52 and secured with locking members from cervical or thoracic screw systems. The double headed connector 60 may be suitable for two rods in the cervical thoracic spine, for example.

Figure 4:
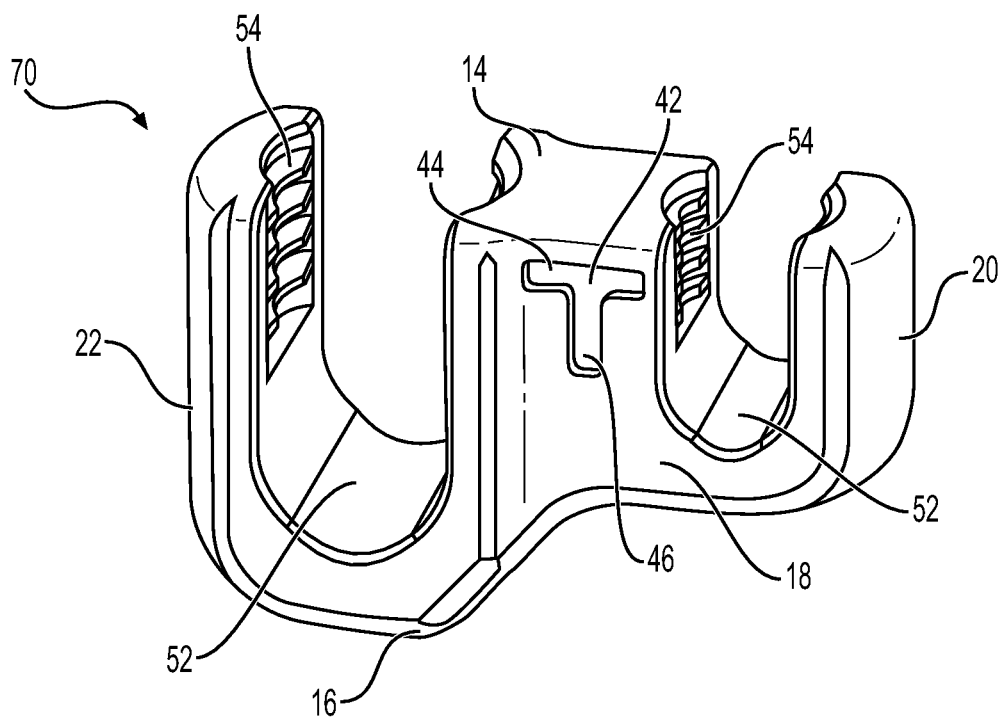
FIG. 4 shows a perspective view of a double headed parallel connector for accepting rods of different sizes according to one embodiment.

Referring now to FIG. 4, a parallel connector or implant 70 is shown according to one embodiment. Similar to implant 60, implant 70 includes a double connector with two rod slot 52 for receiving the rods and the T-shaped engagement recesses 42 for engaging with an inserter instrument. In this implant 70, one rod slot 52 is larger than the other. The larger rod slot 52 is configured to accommodate a larger rod from the thoracolumbar spine and the smaller rod slot 52 is configured to accommodate a smaller rod from the cervical thoracic spine, for example.

For double headed implant 70, the bottom surface 16 of the implant 70 may be stepped downwards to accommodate the larger rod slot 52. Similarly, the side surfaces 18 may be stepped outwards to accommodate the larger rod slot 52. When two headed partials are used together in this manner, the rod slots 52 may be aligned in parallel or angulated if desired. Any angulation may occur in cephalad/caudal or medial/lateral directions. The rods may be top-loaded into the rod slots 52 and secured with threaded locking members or set screws.

Figure 5:
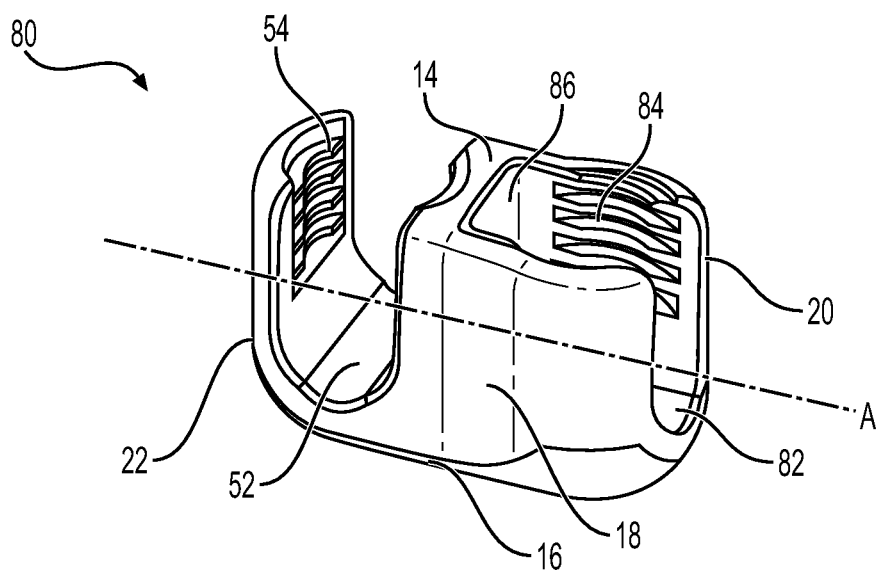
FIG. 5 shows a perspective view of a perpendicular connector according to one embodiment.

Turning now to FIG. 5, a perpendicular connector or implant 80 is shown according to one embodiment. Similar to implants 60, 70, implant 80 includes a headed portion including rod slot 52 for receiving one rod. Implant 80 also includes a perpendicular headed portion for receiving a perpendicular rod.

The perpendicular headed portion may also include a tulip with two opposing sides spaced apart by a rod slot 82 configured to receive one of the spinal rods. In this embodiment, the perpendicular rod slot 82 is oriented in line with a longitudinal axis A of the implant 80 extending between the front 20 and rear 22 of the implant 80. In this manner, a rod positioned in rod slot 82 is oriented perpendicular to a rod positioned in slot 52. The front 20 of the implant 80 is open to receive the perpendicular rod. The rod may be top-loaded or side-loaded into the rod slot 82. The opposing sides of the tulip head may define internal threads 84 configured to mate with the exterior threads on a locking member, thereby securing the rod in the rod slot 82. A central wall 86 may separate the rod slots 52, 82 from one another. The two headed partials of the perpendicular connector 80 allows for great variability in the construct.

Figure 6:
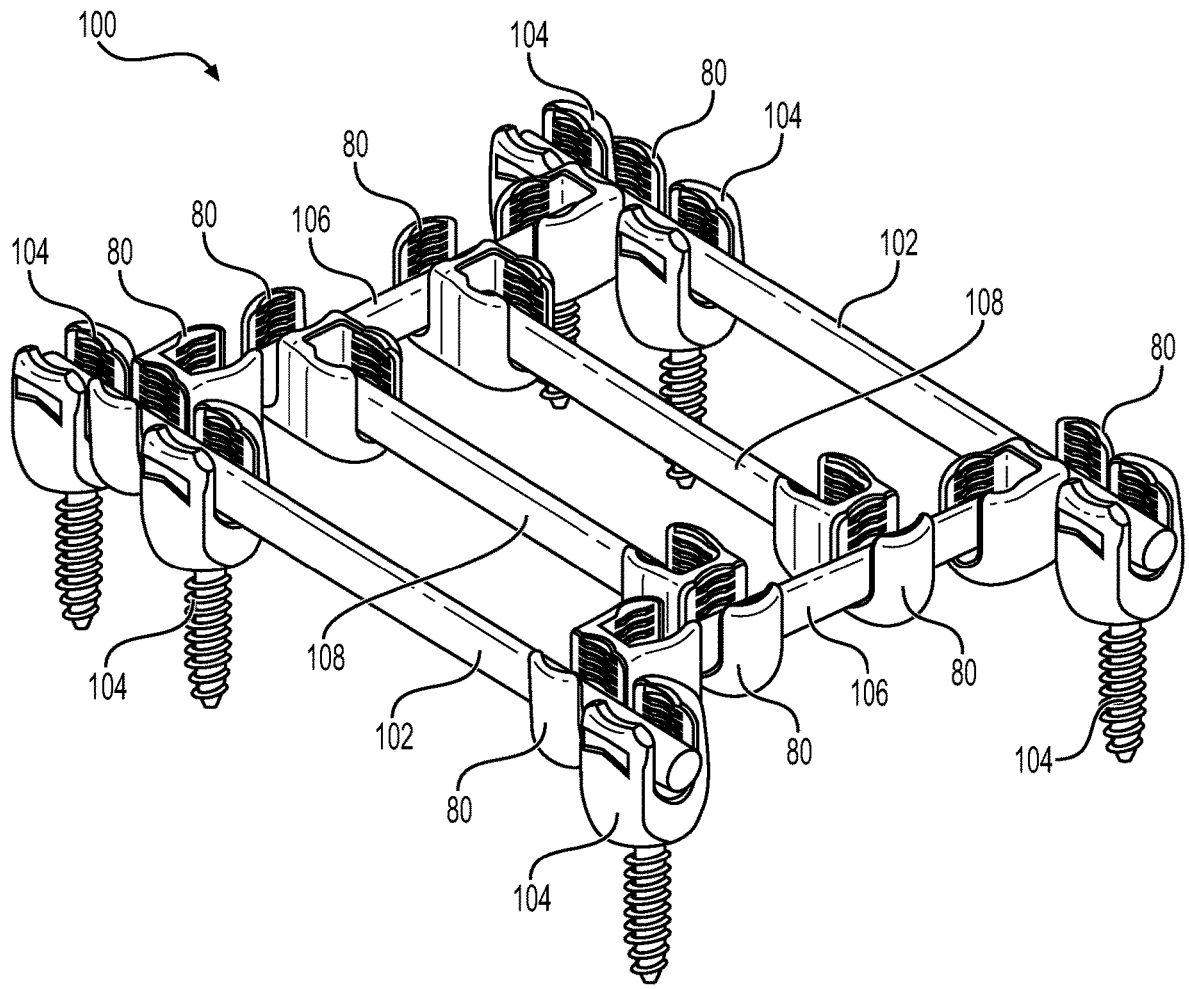
FIG. 6 shows an example of a construct with two cervical rods augmented with additional rods using the perpendicular connectors of FIG. 5.

With reference to FIG. 6, an example of a construct 100 is shown according to one embodiment. In this example, a fixation system may include two cervical rods 102 fixated to the cervical spine with a plurality tulip-style fasteners 104. As shown, a first cervical rod 102 may be secured by three fasteners 104 to left pedicles and a second cervical rod 102 may be secured by three fasteners 104 to right pedicles during a posterior fusion procedure. During the initial procedure or in a subsequent revision procedure, the cervical rods 102 may be augmented with one or more additional rods 106, 108.

For example, the surgeon may build one or more cross-connectors 106 using two perpendicular connectors 80 at each end of the cross-connector rod 106. As shown, rods 102 may be positioned in rod slots 52 and each end of the cross-connector rod 106 may be positioned in the rod slots 82 in connectors 80. At the superior end of the construct, a first perpendicular connector 80 may be nested between the two fasteners 104 on the left side and a second perpendicular connector 80 may be nested between the two fasteners 104 on the right side. The first cross-connector rod 106 is positioned therebetween. Similarly, at the inferior end of the construct, a third perpendicular connector 80 may be positioned next to the fastener 104 on the left side and a fourth perpendicular connector 80 may be positioned next to the fastener 104 on the right side. The second cross-connector rod 106 is positioned therebetween.

With two cross-connector rods 106 in place, the surgeon may further strengthen a construct by adding one or more vertical struts 108 using the connectors 80 on the cross-connector rods 106. As shown, cross-connector rods 106 may be positioned in rod slots 52 and each end of the vertical rods 108 may be positioned in the rod slots 82 in connectors 80. For example, a fifth perpendicular connector 80 may be positioned along the first connector rod 106 and a sixth perpendicular connector 80 may be positioned along the second connector rod 106. The first vertical strut 108 is positioned therebetween. Similarly, a seventh perpendicular connector 80 may be positioned along the first connector rod 106 and an eight perpendicular connector 80 may be positioned along the second connector rod 106. The second vertical strut 108 is positioned therebetween. The first and second vertical struts 108 may be aligned generally in parallel with the two cervical rods 102. A suitable number of connectors 80 and rods 106, 108 may be selected by the surgeon to achieve the desired construct.

The suite of connectors 10, 50, 60, 70, 80 may be used in any combination of the partial connections, including two of the same, in the manner described herein. These connectors 10, 50, 60, 70, 80 allow for fixating two rods together to extend existing or revising constructs. The connectors 10, 50, 60, 70, 80 may be sized to accept rods in the following ranges, for example: cervical-thoracic (3.2-4.0 mm), thoracolumbar small (4.5-5.0 mm), and thoracolumbar (5.5-6.35 mm).

Figure 7:
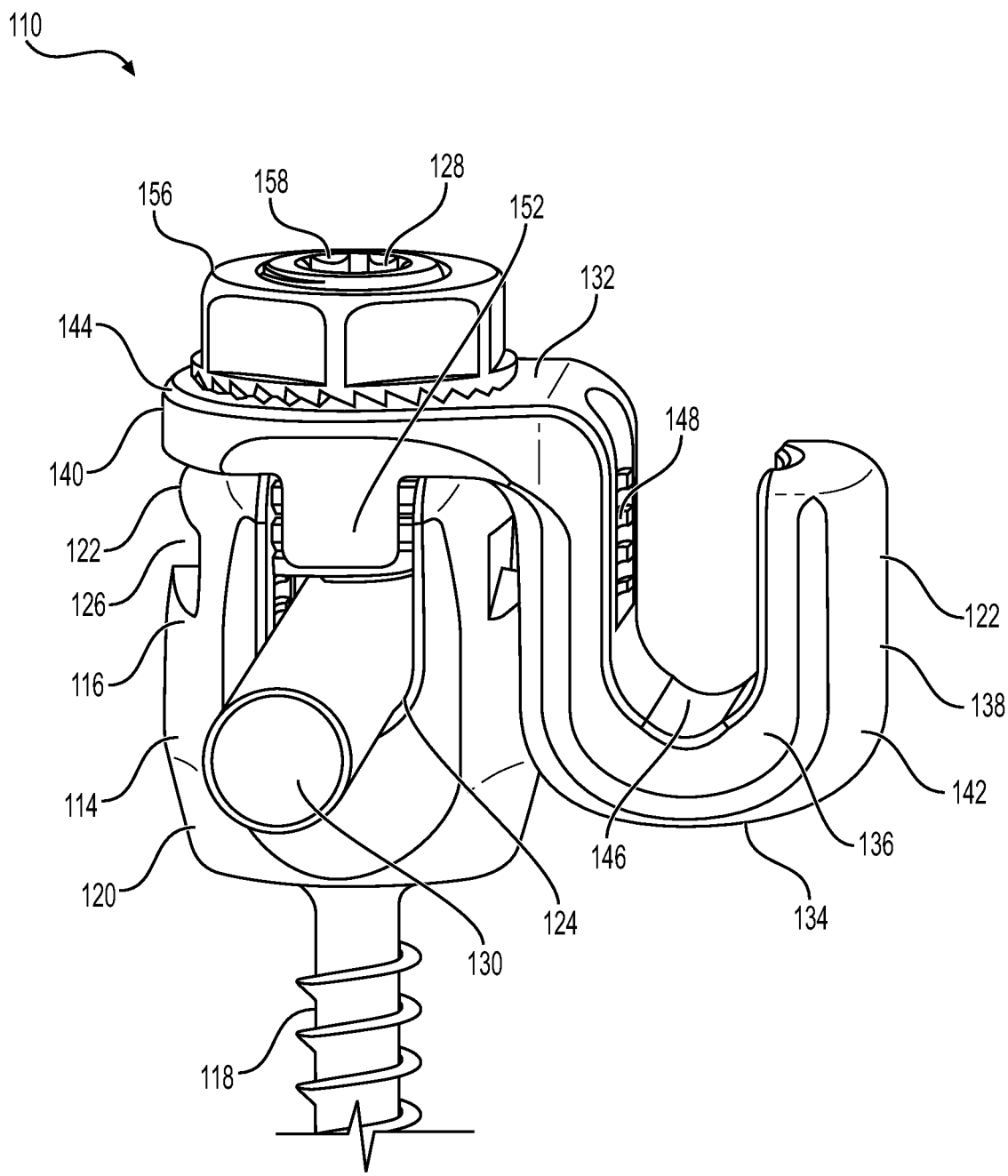
FIG. 7 shows a perspective view of an assembly with a screw-based connector coupled to a tulip head configured for accepting a parallel rod according to one embodiment.

Turning now to FIG. 7, a fastener-based connector assembly 110 is shown according to one embodiment. In this embodiment, the connector 112, also termed a zero-run-on-rod or ZROR connector 112, does not connect directly to one of the rods. Instead, the connector 112 couples directly to the head 116 of the fastener 114, which secures the rod 130 therein. The connector 112 places a headed partial next to the existing screw head 116, and is thereby configured to connect a second rod to the existing rod in the fastener 114.

The fastener 114 may include a tulip element or tulip head 116 and a bone fastener 118. The tulip head 116 may include a body 120 and arms 122 that extend upwardly from the body 120. The opposed arms 122 may define a U-shaped channel or rounded rod slot 124 sized and configured to accept the spinal rod 130. Each of the arms 122 may include an outer surface with tool engagement grooves 126 used for holding the tulip head 116 with a suitable tool. Each of the arms 122 may have an interior surface with a threaded portion for engaging a locking cap post 128.

The bone fastener 118 may include a bone screw, anchor, clamp, or the like configured to engage bone. In the embodiment shown, the bone fastener 118 is a bone screw, such as a pedicle screw, having a screw head and a threaded shaft (the tip of the shaft is omitted from FIG. 7). It will be appreciated that the threaded shaft may have a number of different features, such as thread pitch, shaft diameter to thread diameter, overall shaft shape, and the like, depending, for example, on the particular application. The fastener 114 may be a polyaxial fastener to allow for rotational movement and/or angular adjustment of the bone fastener 118 with respect to the tulip head 116. It will be appreciated that the fastener 114 may also be uniplanar, monoaxial, or other suitable screw type. Examples of bone fasteners are described in more detail, for example, in U.S. Pat. No. 10,368,917, which is incorporated by reference herein in its entirety for all purposes.

The connector 112 has a body with an upper surface 132, a lower surface 134, opposed side surfaces 136, a nose or front surface 138, and a back or rear surface 140. The connector 112 includes two coupling portions. The first portion 142 includes a headed portion similar to implant 60, 70. The headed portion 142 of the connector 112 may be in the form of a tulip with two opposing sides spaced apart by a rod slot 146 configured to receive the spinal rod. A rod may be top-loaded into the rod slot 146. The opposing sides of the tulip head may define internal threads 148 configured to mate with the exterior threads on a locking member or set screw to secure the rod therein. The rod may be captured in three point contact due to the dual diameter of the bottom of the rod slot 146.

Figure 8A:
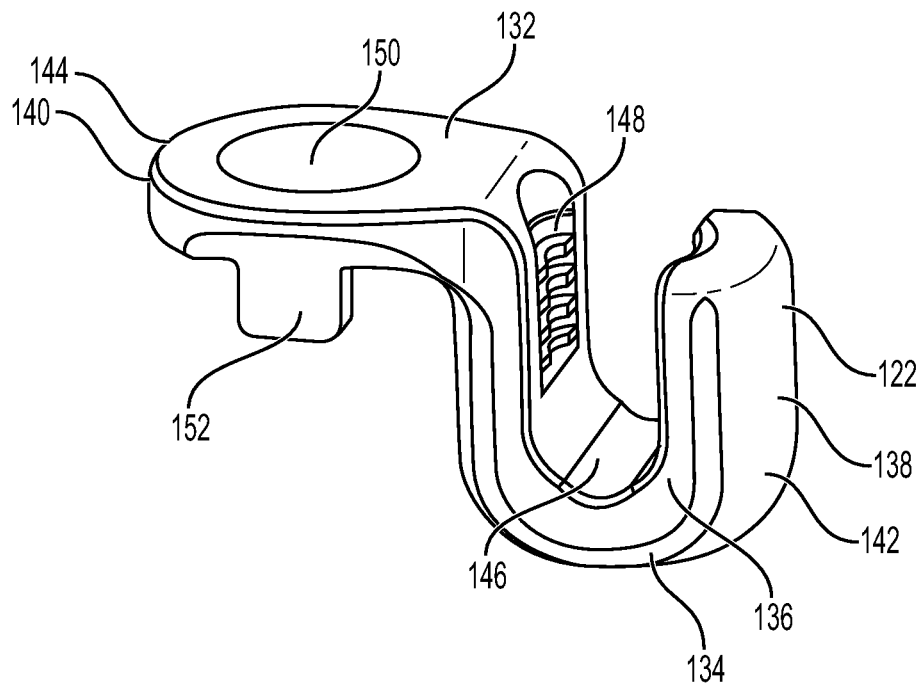
FIGS. 8A-8B show front and lower perspective views, respectively, of the screw-based connector shown in FIG. 7.
Figure 8B:
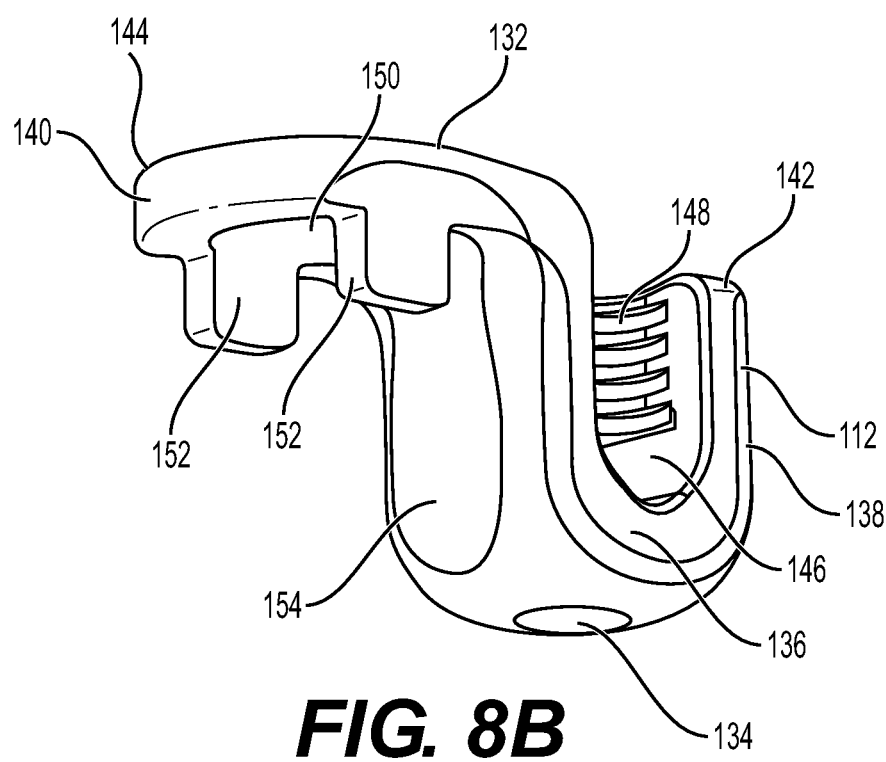

With emphasis on FIGS. 8A-8B, the second portion 144 of the connector 112 is configured to engage the head 116 of the pedicle screw 114. The second portion 144 of the connector 112 defines a thru hole 150 configured to accept a portion of the locking cap post 128. The thru hole 150 may be non-threaded. The second portion 144 may include one or more tabs or prongs 152. For example, the second portion 144 may include two opposed prongs 152 extending downwardly on opposite sides of the thru hole 150. The prongs 152 may be configured to engage the rod slot 124 of the fastener 114. For example, the two prongs 152 may sit inside the rod slot 124 of the existing screw 114 to limit the angle of the adjacent rod. The angle may be limited to ±5 degrees, for example. As best seen in FIG. 8B, a cutout 154 on the inside of the connector 112 provides for clearance of the existing screw 114, thus allowing for minimal offset distance.

As best seen in FIG. 7, the rod 130 may be secured in the tulip head 116 with the posted locking cap 128. The posted locking cap 128 may include a body with an upper surface, a lower surface, and an outer body defining a threaded portion. The posted locking cap 128 may be in the form of a set screw with a drive feature or recess 158 defined in the upper surface configured to be engaged by a driving instrument, which is able to insert and tighten the locking cap 128 in the tulip head 116. The recess 158 may be a hexalobe, slot, cross, or other suitable shape that may engage with a tool or device having a corresponding recess. The bottom of the locking cap 128 may be flat or otherwise configured to ensure consistent contact with the rod 130.

The connector 112 is attached to the existing screw 114 using the posted locking cap 128 and locking nut 156. The connector 112 sits on the top of the tulip head 116 and is clamped down onto it by using the locking nut 156. The locking cap post 128 is positioned through opening 150 and into contact with the rod 130 positioned in the slot 124 in the head 116 of the fastener 114. The locking cap post 128 may include outer threads that mate with the tulip threads and the locking nut threads. The locking cap post 128 may be dual-threaded with two distinct threaded portions of different thread types, diameters, or the like. The locking nut 156 may be secured to an upper portion of the locking cap post 128. The locking nut 156 has an internal thread for engagement with an upper threaded portion of the locking cap post 128.

The outer geometry of the nut 156 (e.g., a hex nut) is such that the nut 156 may be driven by an instrument. The bottom surface of the locking nut 156 contacts the upper surface 132 of the connector 112 to secure the connector 112 to the fastener 114. The locking nut 156 may have teeth or a roughened surface cut into the bottom face to prevent loosening or it may be flat/smooth for maximum contact area. The connector 112 is secured to the fastener 114 via the force applied by the locking nut 156. The prongs 152 on the connector 112 may allow the connector 112 to remain stable in torsion during tightening by preventing rotation of the connector 112.

Figure 9:
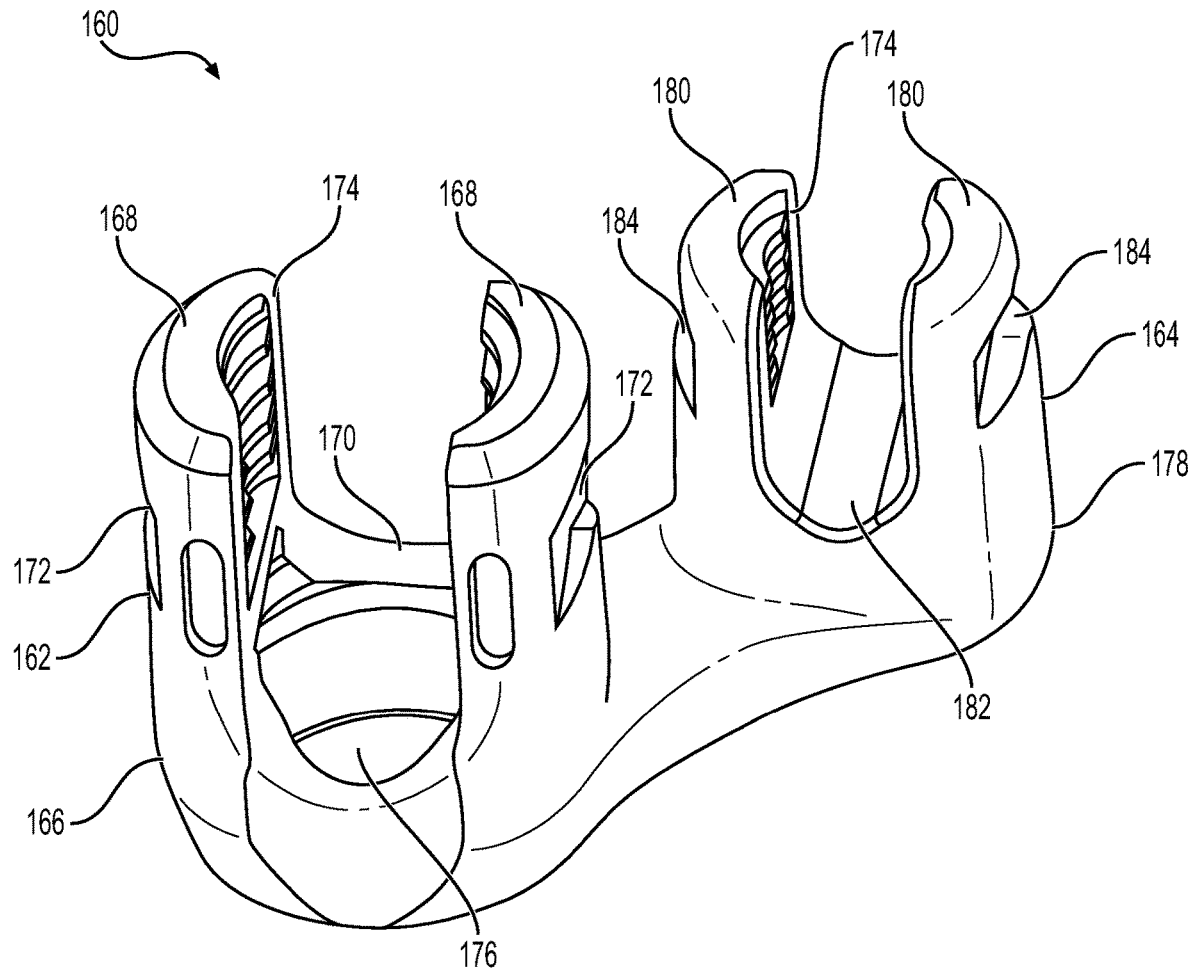
FIG. 9 shows a connector configured to attach to a screw head according to one embodiment.

Turning now to FIG. 9, a connector or implant 160 is shown according to one embodiment. Similar to implant 60, implant 160 includes a double connector with two rod slots 170, 182 for receiving the rods. The rod slots 170, 182 may be separate and offset from one another. The first portion 162 includes a head portion 166 configured to attach to a screw head and receive a first rod and the second portion 164 is configured to receive a second rod.

The first portion 162 of the implant 160 may include a first tulip element or tulip head 166 configured to secure a bone fastener. The tulip head 166 may include a body and arms 168 that extend upwardly from the body. The opposed arms 168 may define a U-shaped channel or rod slot 170 sized and configured to accept one spinal rod. Each of the arms 168 may include an outer surface with one or more tool engagement grooves 172 used for holding the tulip head 166 with a suitable tool (not illustrated). Each of the arms 168 may have an interior surface with a threaded portion 174 for engaging a locking member, such as a set screw. The head 166 defines a central opening 176 transverse and in fluid communication with the rod slot 170. The central opening 176 may be configured to accept a portion of a fastener, such as a screw head. The tulip head 166 may secure the screw head with a locking assembly, such as a saddle and clamp. Examples of these are described in U.S. Pat. No. 10,368,917, which is incorporated by reference herein in its entirety for all purposes.

The second portion 164 of the implant 160 may include a second tulip element or tulip head 178 separate and offset from the first tulip head 166. The tulip head 178 may include a body and arms 180 that extend upwardly from the body. The opposed arms 180 may define a U-shaped channel or rod slot 182 sized and configured to accept another spinal rod. The rod may be captured in three-point contact due to the dual diameter of the bottom of the rod slot 182. Each of the arms 180 may include an outer surface with one or more tool engagement grooves 184 used for holding the tulip head 178 with a suitable tool. Each of the arms 180 may have an interior surface with a threaded portion 174 for engaging a locking member, such as a set screw, to thereby secure the rod in the head 178.

The connector 160 is configured to secure two spinal rods to a screw head. The rod slots 170, 182 may be oriented parallel to one another or may be angulated relative to each other in either cephalad/caudal or medial/lateral directions. The rod slots 170, 182 may be the same or different sizes. In this embodiment, rod slot 170 is larger and deeper than rod slot 182, which is smaller and shallower. For example, rod slot 170 may be sized and configured to secure a larger thoracolumbar rod, and rod slot 182 may be sized and configured to secure a smaller cervical rod.

Figure 10:
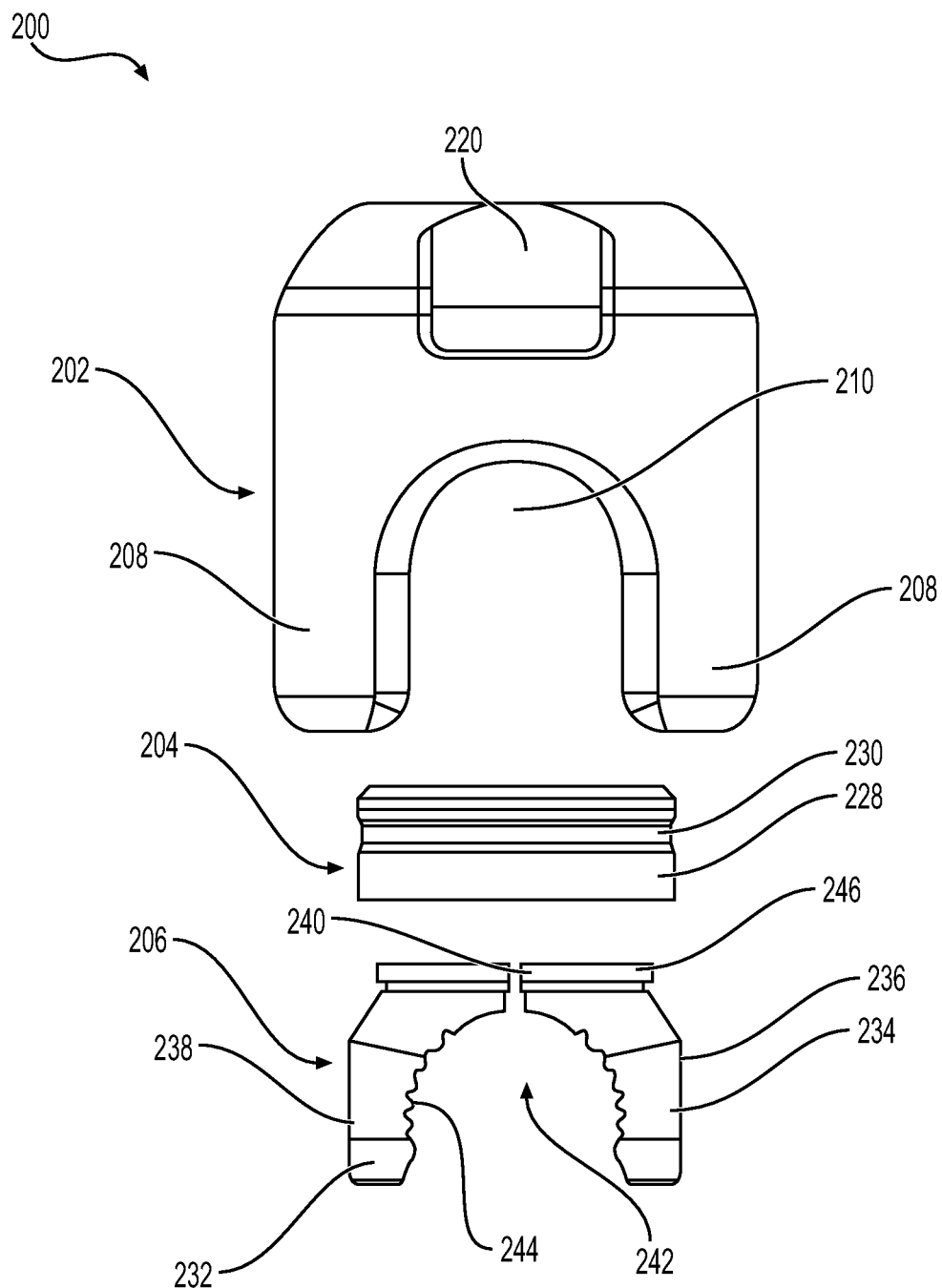
FIG. 10 is an exploded view of a top loading connector portion configured to attach to a rod according to one embodiment.

Turning now to FIG. 10, an exploded view of a top loading connector portion 200 is shown according to one embodiment. A resulting connector may include the top loading portion 200 for attachment onto a first spinal rod adjacent and a second portion for attachment onto a second spinal rod. The top loading portion 200 attaches onto the first spinal rod from above while the second connector portion may attach onto the second spinal rod in one of several embodiments.

Figure 13:
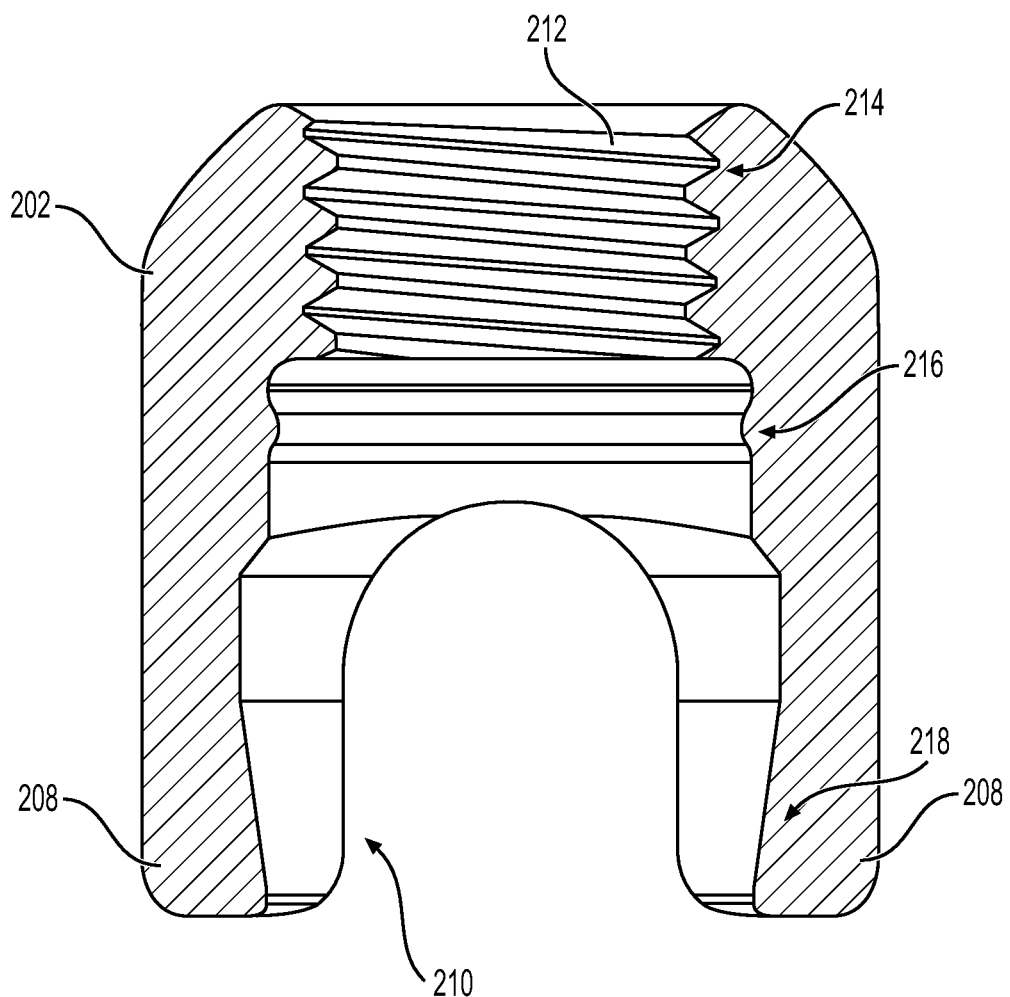
FIG. 13 shows a cross-section of the main body of the top loading connector portion according to one embodiment.

With emphasis on FIG. 10, the top loading connector portion 200 includes a housing or main body 202, a saddle 204, and a clamp 206. As best seen in FIG. 13, the main body 202 includes two opposed arms 208 which define a rod slot 210 therebetween. An opening 212 extends through the body 202 to intersect rod slot 210. Opening 212 may be transverse or perpendicular with the rod slot 210. An upper portion of the opening 212 includes a threaded portion 214 defining internal threads and a lower portion of the opening 212 defines one or more tapered inner surfaces 218. A modular bump 216 may be located between the threaded portion 214 and the tapered inner surface 218. An outer surface of the main body 202 may define one or more engagement recesses 220 for engagement with an insertion instrument. For example, two opposed engagement recesses 220 may be defined within the side surfaces near the top of the top loading connector portion 200.

Figure 11A:
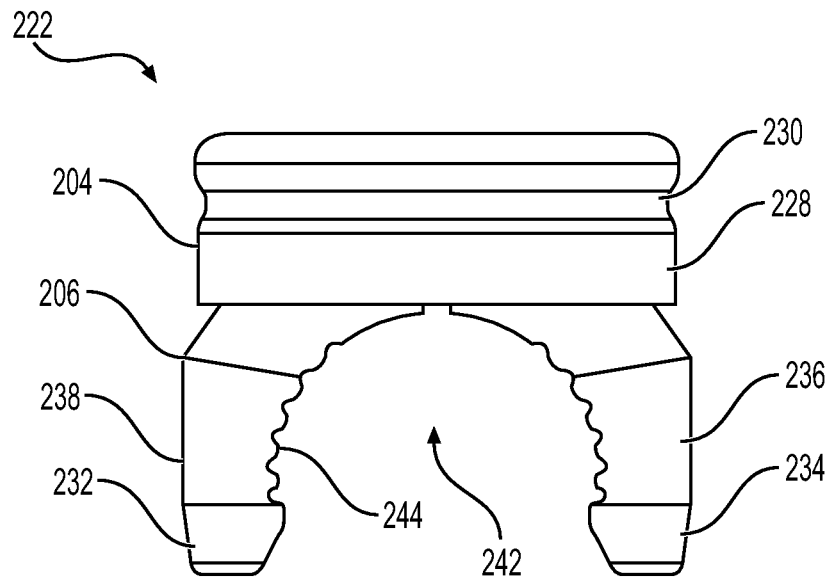
FIGS. 11A-11B show side and cross-sectional views, respectively, of the saddle and clamp of the top loading connector portion of FIG. 10.
Figure 11B:
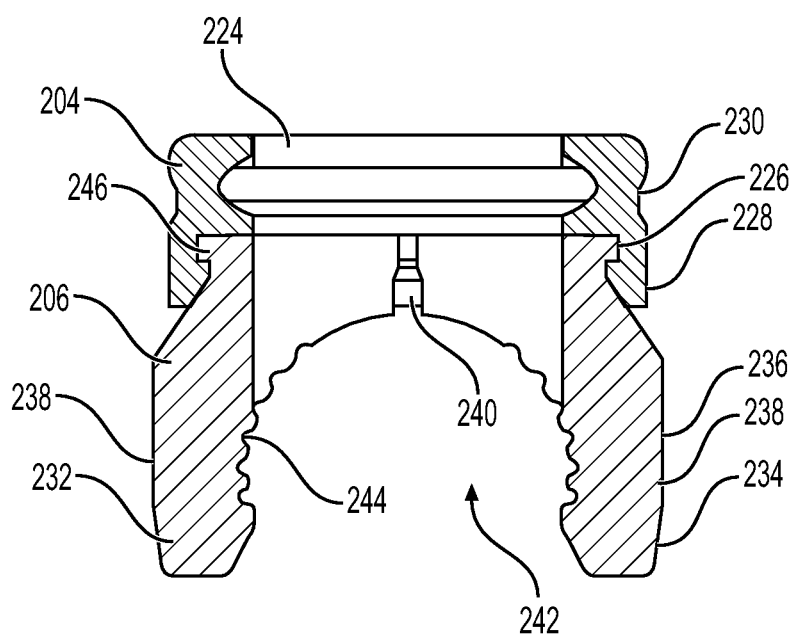

With emphasis on FIGS. 11A-11B, the clamp 206 engages with the saddle 204 to create a locking assembly 222 to secure the rod 250. The saddle 204 may include a ring-like body with a bore 224 extending therethrough. A lower portion of the bore 224 may be sized to receive an upper portion of the clamp 206. For example, an inner annular groove 226 may be defined within the bore 224 to secure the clamp 206. The saddle 204 may include an outer surface 228 having a recessed portion or outer annular groove 230. The outer surface 228 may be generally rounded, for example. The outer surface 228 of the saddle 204 may be generally elliptical in shape, in one embodiment.

As best seen in FIG. 11B, the clamp 206 may be split into two pieces: a first clamp portion 232 and a second clamp portion 234 separated by at least one slit 240. The first and second clamp portions 232, 234 include an outer surface 236, which may be curved or rounded. A lower portion of the outer surface 236 of the first and second clamp portions 232, 234 may include a tapered outer surface 238. The tapered outer surface 238 abuts and engages the tapered inner surface 218 of the body 202. A collar or ledge 246 may be provided at the top of the clamp 206. The ledge 246 is receivable in the groove 226 in the saddle 204 to secure the clamp 206 to the saddle 204. The first and second clamp portions 232, 234 define an inner surface or rod slot 242 configured to clamp about the spinal rod, when installed.

The two halves 232, 234 of the clamp 206 may be permitted to snap around the spinal rod. The illustrated embodiment shows the inner surfaces or rod slot 242 having roughened or textured features 244 that improve engagement with the rod.

In the illustrated embodiment, the first clamp portion 232 is substantially identical to and a mirror image of, the second clamp portion 234. While the embodiments that are described and illustrated generally describe the first and second clamp portions 232, 234 as substantially identical, the portions 232, 234 may be of varying size and are not required to be mirror images of one another. In addition, while the clamp 206 is illustrated as having two clamp portions (first and second clamp portions 232, 234), the clamp 232 may comprise more than two portions for gripping the rod.

Figure 12A:
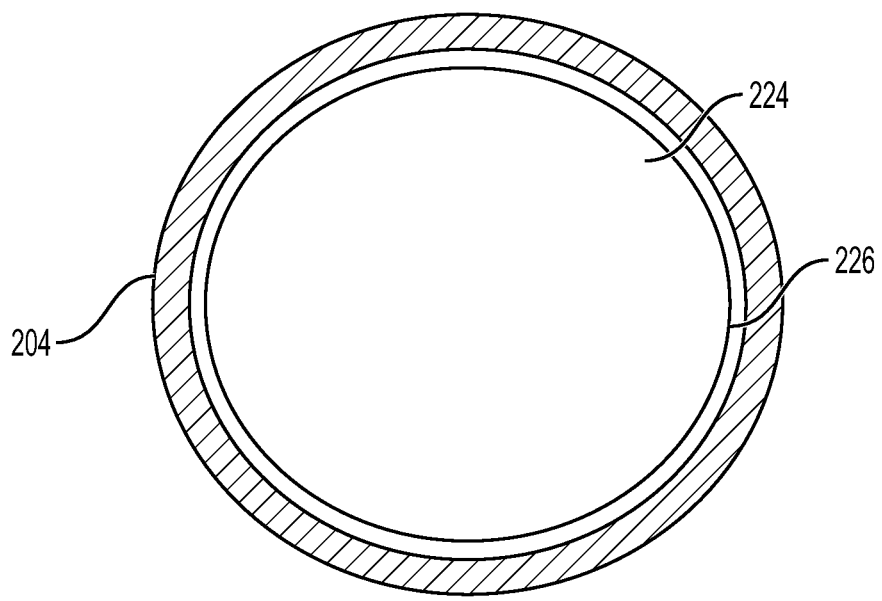
FIG. 12A shows a lower groove in the saddle and FIG. 12B shows an upper ledge of the clamp configured to mate with the groove in the saddle according to one embodiment.
Figure 12B:
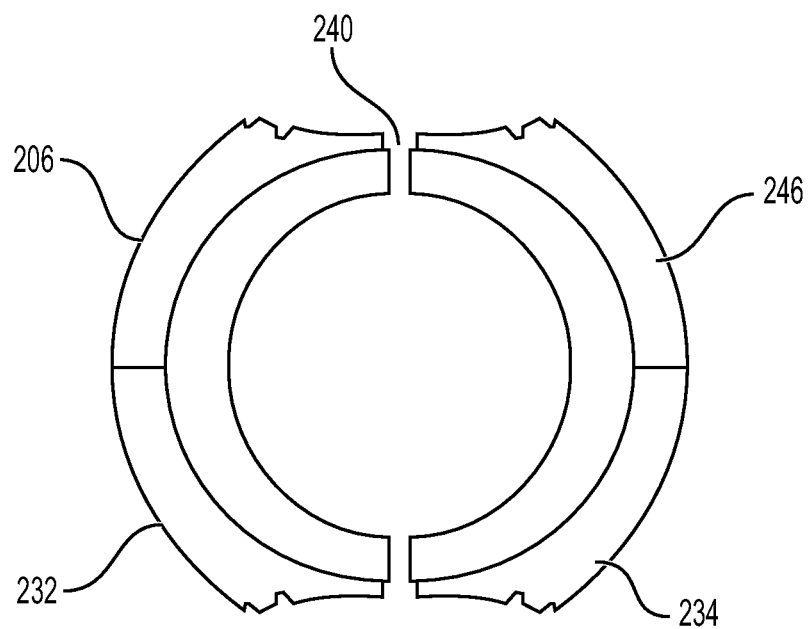

With emphasis on FIGS. 12A-12B, the mating surfaces of the clamp 206 and saddle 204 may be elliptical in shape. FIG. 12A shows the lower groove 226 in the saddle 204 is elliptical in shape. FIG. 12B shows the upper ledge 246 of the clamp 206 has a mating elliptical shape. The groove 226 in the saddle 204 is configured to accept the ledge 246 of the clamp 206. The elliptical shape keeps the two components 204, 206 oriented in a specific orientation with respect to one another.

Figure 14A:
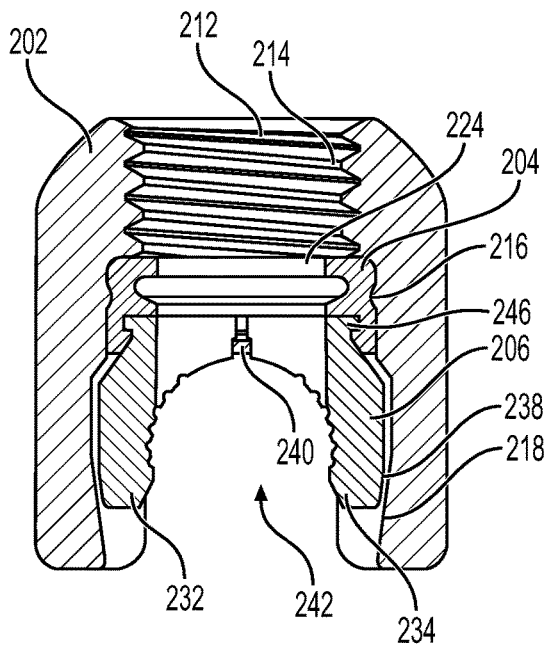
FIGS. 14A-14C show cross-sections of the top loading connector portion, with the saddle and clamp, and engaging a spinal rod in an upward loading position.
Figure 14B:
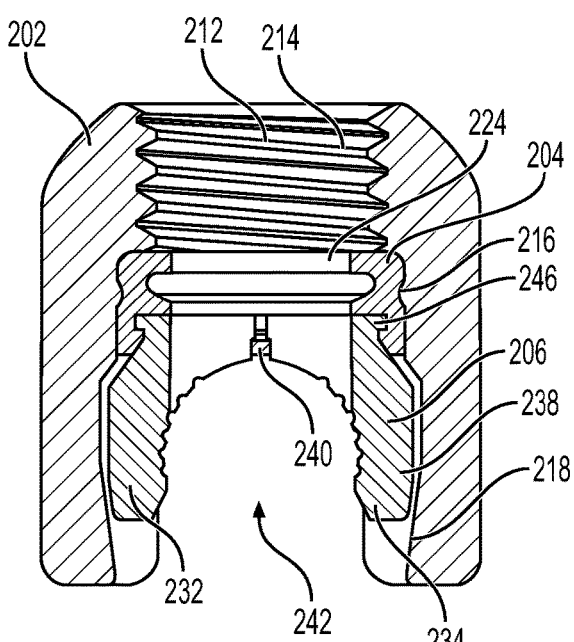
Figure 14C:
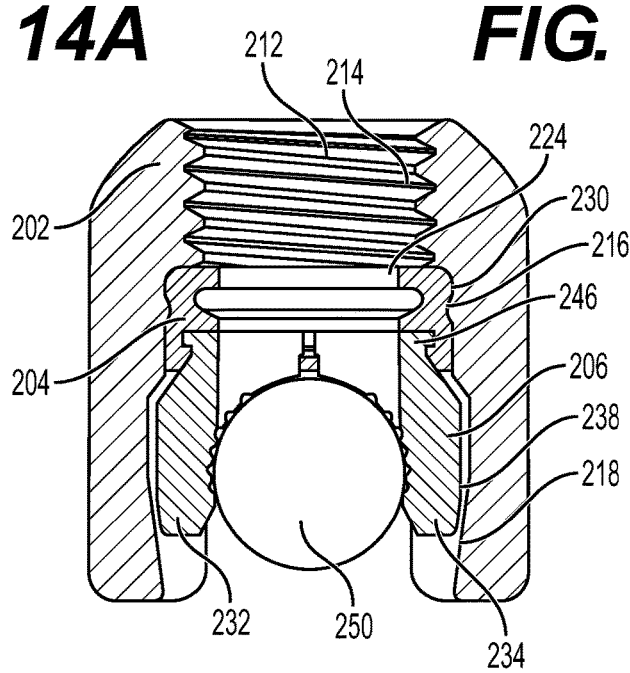

Turning now to FIGS. 14A-14C, the locking assembly 222 may be assembled into the main body 202 from the bottom. The modular bump 216 engages the saddle 204 to create two distinct conditions: an unlocked position and a locked position. FIGS. 14A-14B show the saddle 204 and clamp 206 in an upward or loading position. FIG. 14C shows the two clamp portions 232, 234 of the clamp 206 engaged with a spinal rod 250 in the loading position. When the saddle 204 is above the modular bump 216, the clamp 206 is located within the tapered surface 218 of the main body 202 such that there is enough room for the clamp 206 to expand in order to accept or release the spinal rod 250.

FIGS. 15A-15B show the saddle 204 and clamp 206 in a downward or captured position. FIG. 15C shows the two clamp portions 232, 234 of the clamp 206 engaged with the spinal rod 250 in the locked or captured position. When the saddle 204 is below the modular bump 216, the clamp 206 is located within the tapered surface 218 of the main body 202 such that the clamp 206 cannot expand to accept or release the spinal rod 250.

Figure 16A:
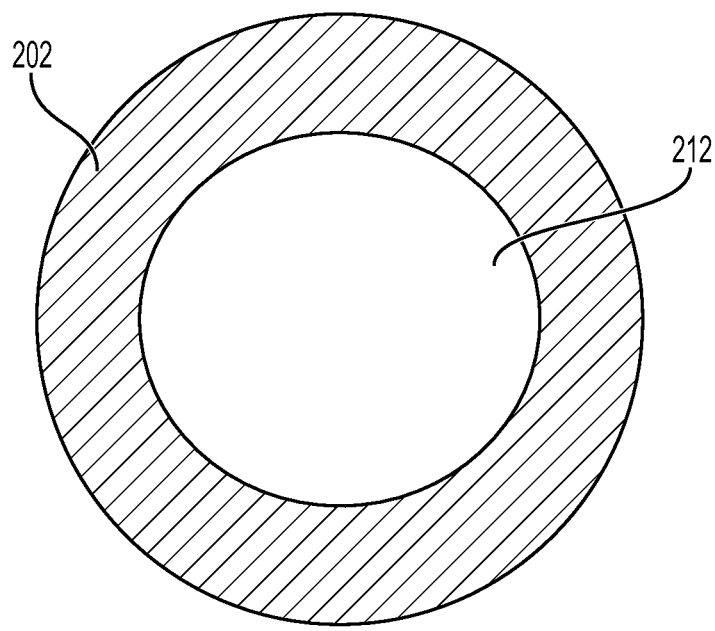
FIG. 16A shows the inner geometry of the main body of the top loading connector portion and FIG. 16B shows the saddle configured to be received in the main body according to one embodiment.
Figure 16B:
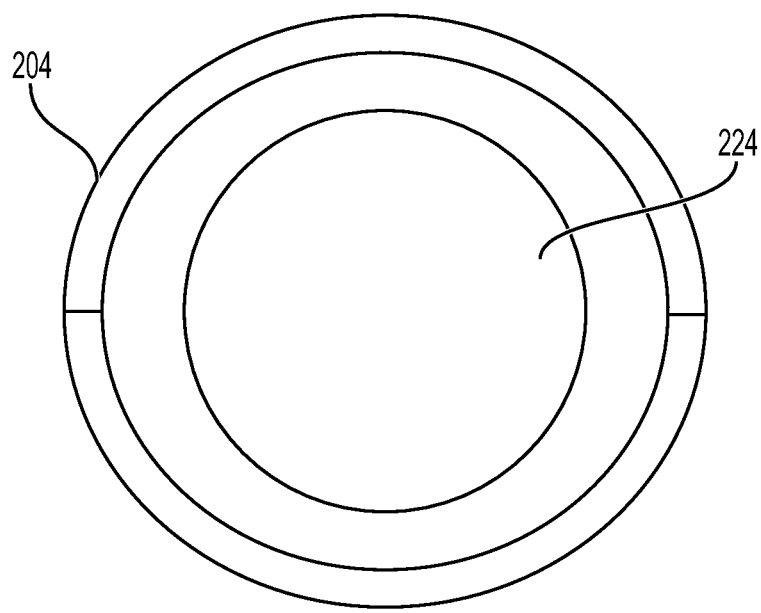

With emphasis on FIGS. 16A-16B, the mating surfaces of the main body 202 and saddle 204 may be elliptical in shape. The inner geometry of the main body 202 may be elliptical in shape to accept the outer surface of the saddle 204, which has a mating elliptical shape. The elliptical shape keeps the two components 202, 204 oriented in a specific orientation with respect to one another. Since the clamp 206 is also oriented within the saddle 204, the result is that the clamp 206 is oriented with respect to the main body 202. This allows the rod slot 210 of the main body 202 and the rod slot 242 of the clamp 206 to be aligned in order to accept the spinal rod 250.

Figure 17A:
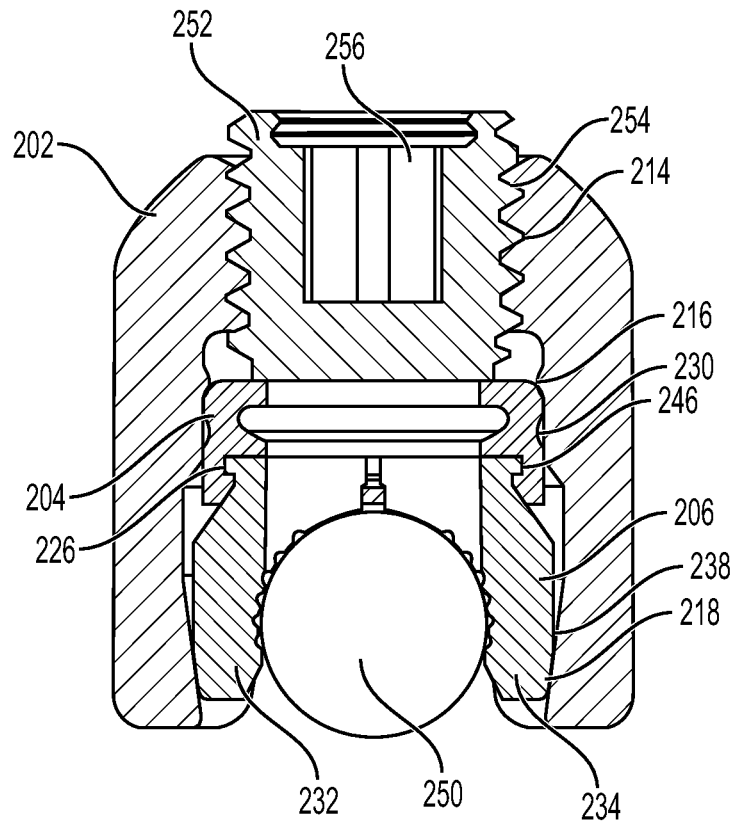
FIGS. 17A-17B show the top loading connector portion with a locking cap in the upward loading position and the downward captured position, respectively.
Figure 17B:
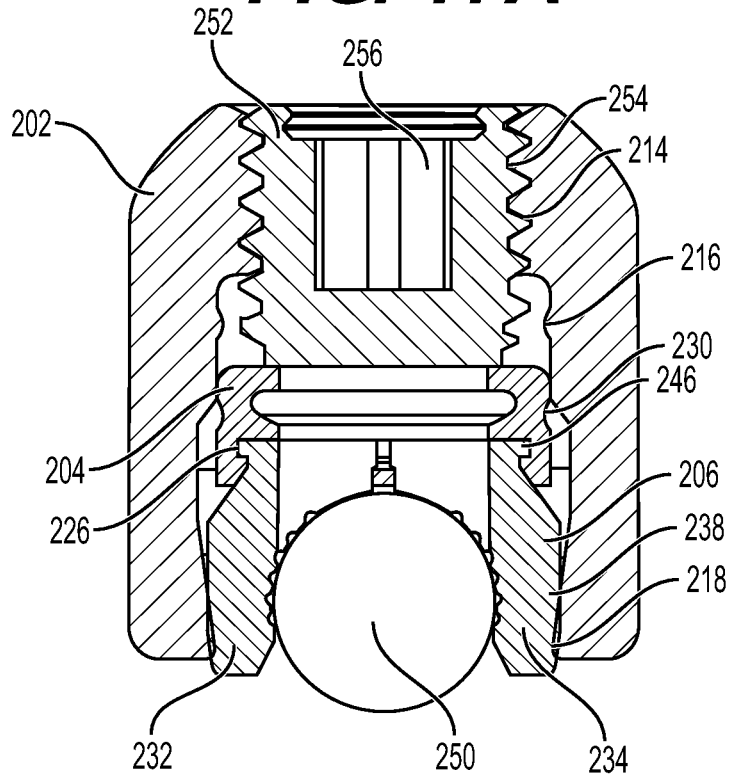

Turning now to FIGS. 17A-17B, the top loading connector portion 200 includes a locking cap 252 configured to translate the clamp 206 downward to secure the spinal rod 250. The locking cap 252 includes an outer threaded portion 254 configured to threadedly mate with the inner threaded portion 214 in the main body 202. The top of the locking cap 252 may include a drive recess 256 configured to be engaged by an instrument, such as a driver, for rotating the locking cap 252.

The inner surface 218 of the main body 202 is tapered such that the diameter decreases from the top to the bottom. The outer surface 236 of the clamp 206 is tapered 238 such that as the clamp 206 translates downward within the main body 202, the inner surface 218 of the main body 202 contacts the tapered outer surface 238 of the clamp 206. This creates a squeezing force to secure the spinal rod 250 within the top loading connector 200. The downward translation of the clamp 206 is achieved with the locking cap 252. The locking cap 252 threads into the main body 202 of the connector portion 200 and contacts the top of the saddle 204. As the locking cap 252 is threaded downward, the clamp 206 translates downward, thereby causing the tapered inner surface 218 of the main body 202 to contact the clamp 206, thus locking the connector portion 200 to spinal rod 250.

The top loading connector portion 200 may be integrated into a number of different connectors with two or more connection portions. FIGS. 18-22 provide some examples of connectors incorporating the top loading connector portion 200. The first connection portion may include the top loading connector portion 200 for attaching onto a first spinal rod 250 and the second connection portion is configured for attachment onto a second spinal rod 250. In this manner, the connector is able to couple two adjacent spinal rods 250. Both rods 250 may be secured during an initial or primary surgery. Alternatively, a second rod 250 may be coupled to a first rod 250 during a subsequent or revision surgery.

Figure 18A:
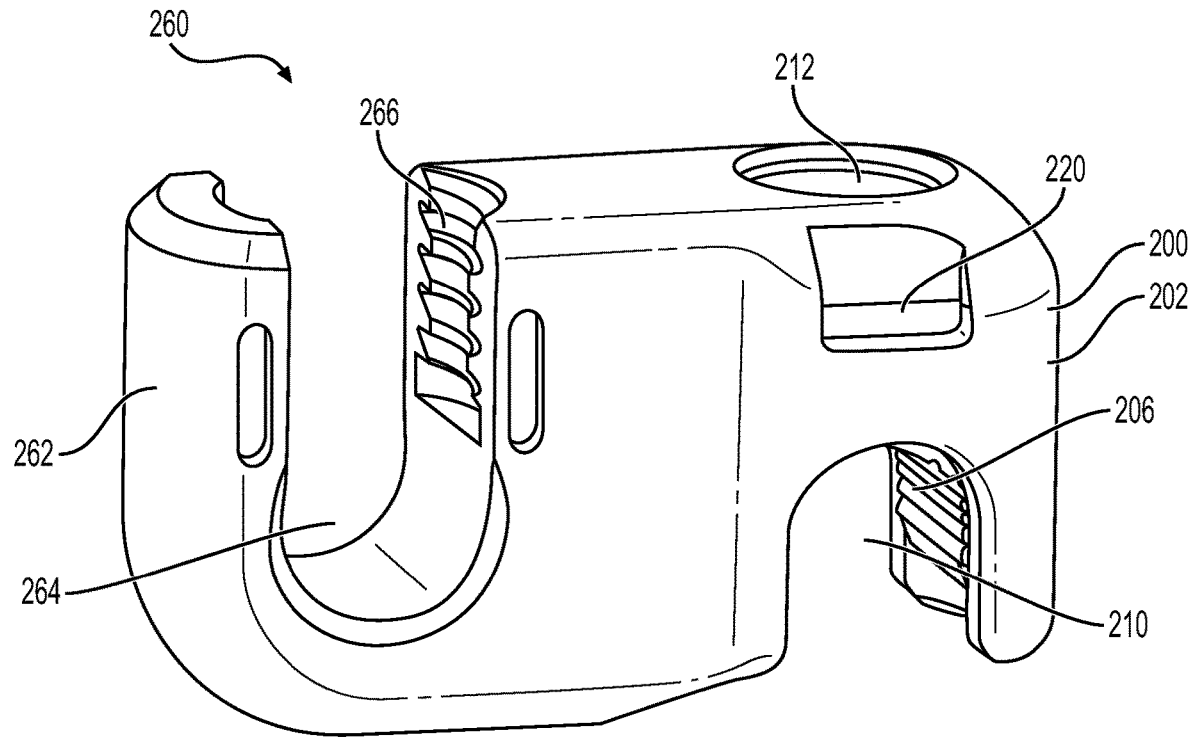
FIGS. 18A-18B show a single head top loading connector and the connector coupling two rods, respectively, according to one embodiment.
Figure 18B:
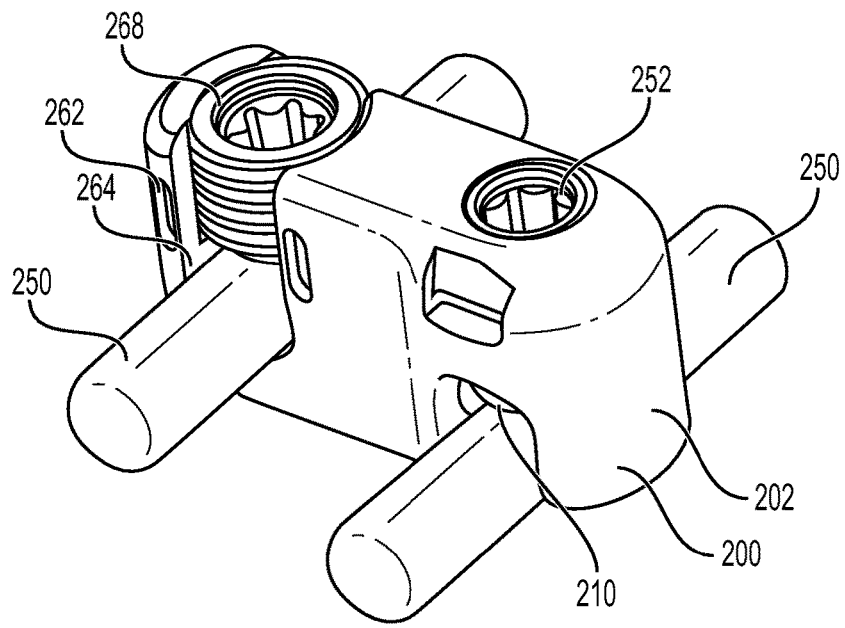

Turning now to FIGS. 18A-18B, a single head top loading connector or implant 260 for coupling two rods 250 is shown according to one embodiment. The single head top loading connector 260 includes the top loading connector portion 200 in parallel with a tulip-style screw head portion 262. The top loading connector portion 200 may form an integral body with the screw head portion 262. The screw head portion 262 includes a U-shaped rod slot 264 configured to accept a spinal rod 250. An upper portion of the rod slot 264 includes a threaded portion defining a plurality of threads 266. The threads 266 engage with a mating threaded locking cap 268. When the locking cap 268 is threaded downward, the cap 268 applies a force against the spinal rod 250 to capture the rod 250 within the rod slot 264 of the connector 260. The rod slots 210, 264 may be aligned in parallel or angulated relative to one another.

Figure 19A:
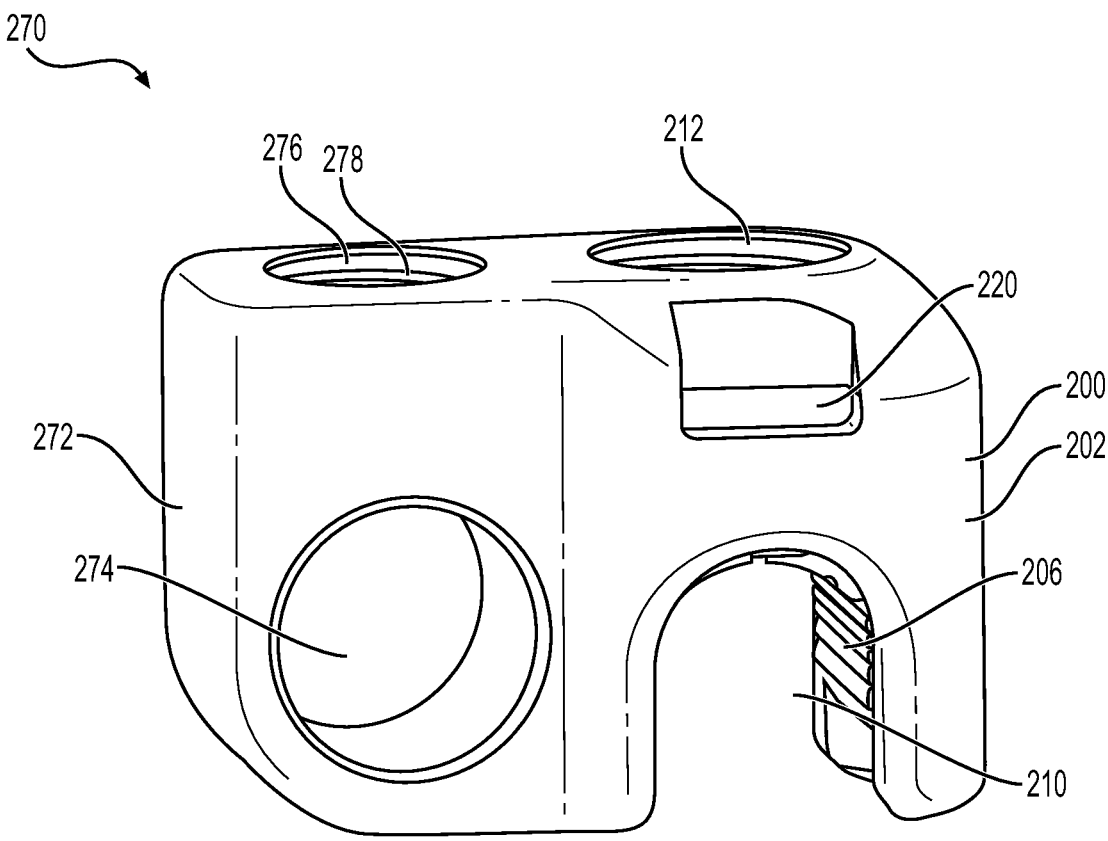
FIGS. 19A-19B show a top loading closed connector and the connector coupling two rods, respectively, according to one embodiment.
Figure 19B:
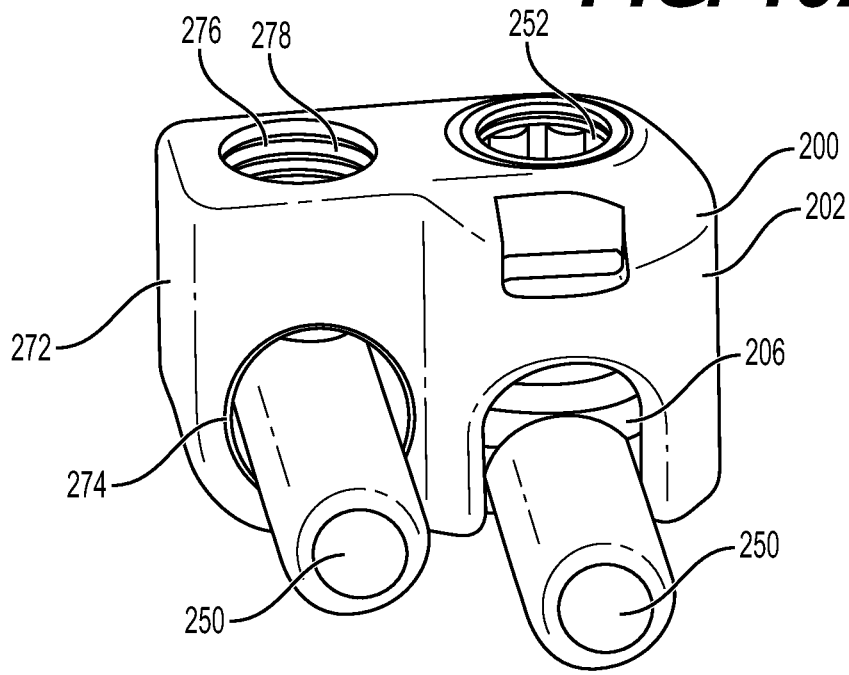

Turning now to FIGS. 19A-19B, a top loading closed connector or implant 270 for coupling two rods 250 is shown according to one embodiment. The top loading closed connector 270 includes the top loading portion 200 in parallel with a closed connection portion 272. The closed connection portion 272 includes a rod slot 274 extending through the body of the connector 270. The closed rod slot 274 is configured to accept one spinal rod 250. The rod slot 274 is closed to fully encircle the rod 250. The rod 250 is radially enclosed by the connector 270 for maximum strength. A perpendicular opening 276 is provided in fluid communication with the rod slot 274. The opening 276 defines threads 278 configured to interface with a locking cap, such as a flat bottom set screw (not shown). The thread 278 engages with the set screw. When the set screw is threaded downward, the flat bottom contacts the spinal rod 250 and applies a force to capture the rod 250 within the rod slot 274 of the connector 270. The rod slots 210, 274 may be aligned in parallel or angulated relative to one another.

Figure 20A:
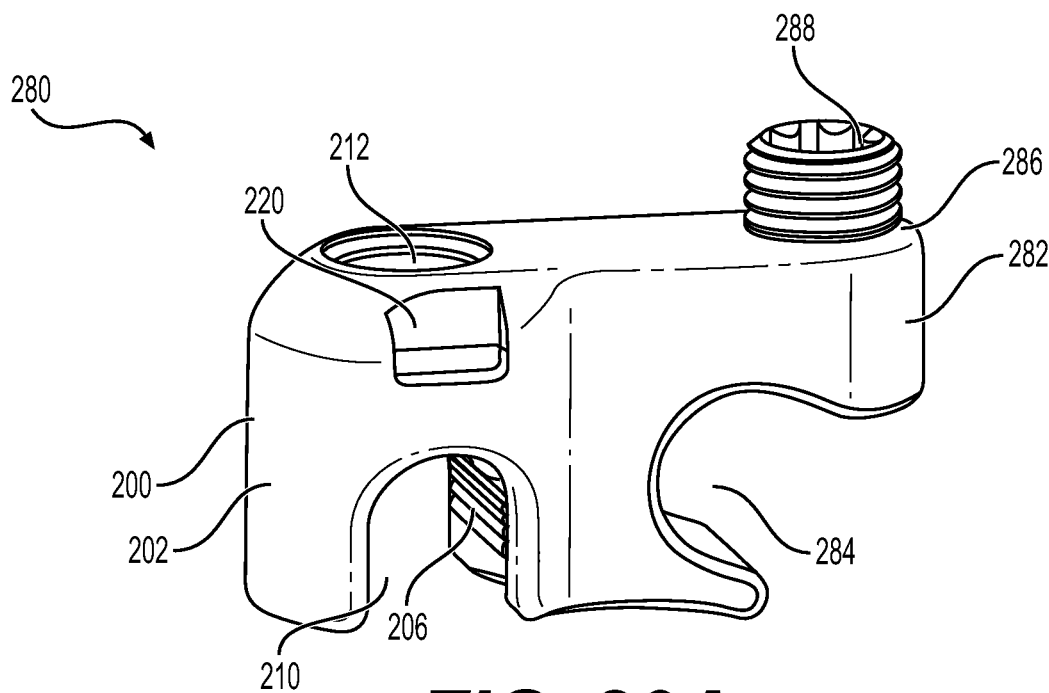
FIGS. 20A-20B show a top loading open connector and the connector coupling two rods, respectively, according to one embodiment.
Figure 20B:
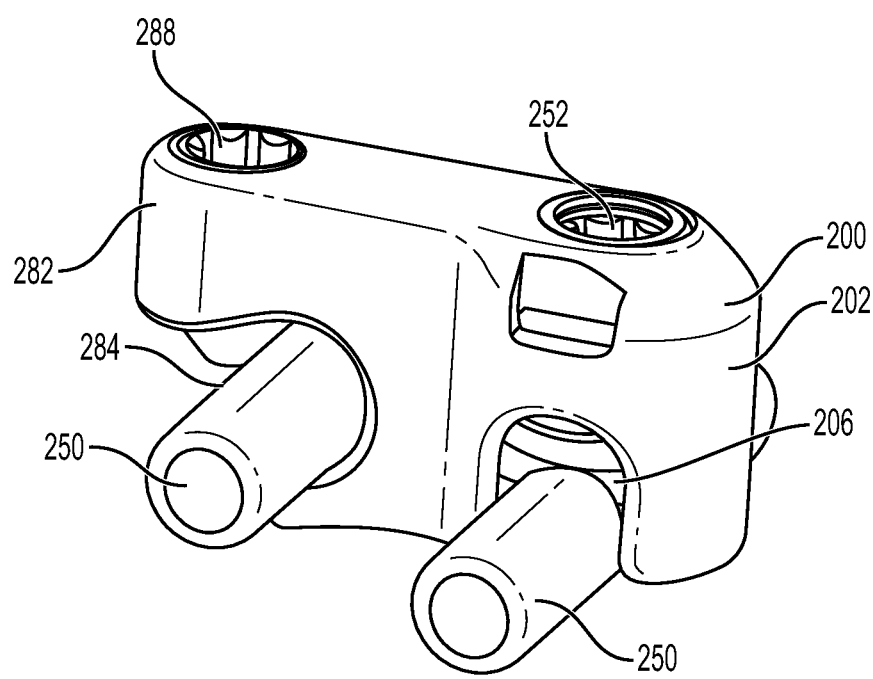

Turning now to FIGS. 20A-20B, a top loading open connector or implant 280 for coupling two rods 250 is shown according to one embodiment. The top loading open connector 280 includes the top loading connector portion 200 in parallel with an open connection portion 282. The open connection portion includes a rod slot 284 configured to accept the spinal rod 250. The rod slot 284 may be an open slot recessed into the front surface of the implant 280. The open slot 284 may define a generally c-shaped recess sized and dimensioned to receive the rod 250 when side-loaded therein. A perpendicular opening 286 intersects with the rod slot 284. The opening 286 defines threads configured to interface with a threaded locking cap 288, such as a conical bottom set screw. When the set screw 288 is threaded downward, the conical surface contacts the spinal rod 250 and applies a force to capture the rod 250 within the rod slot 284 of the connector 280. The rod slots 210, 284 may be aligned in parallel or angulated relative to one another.

Figure 21:
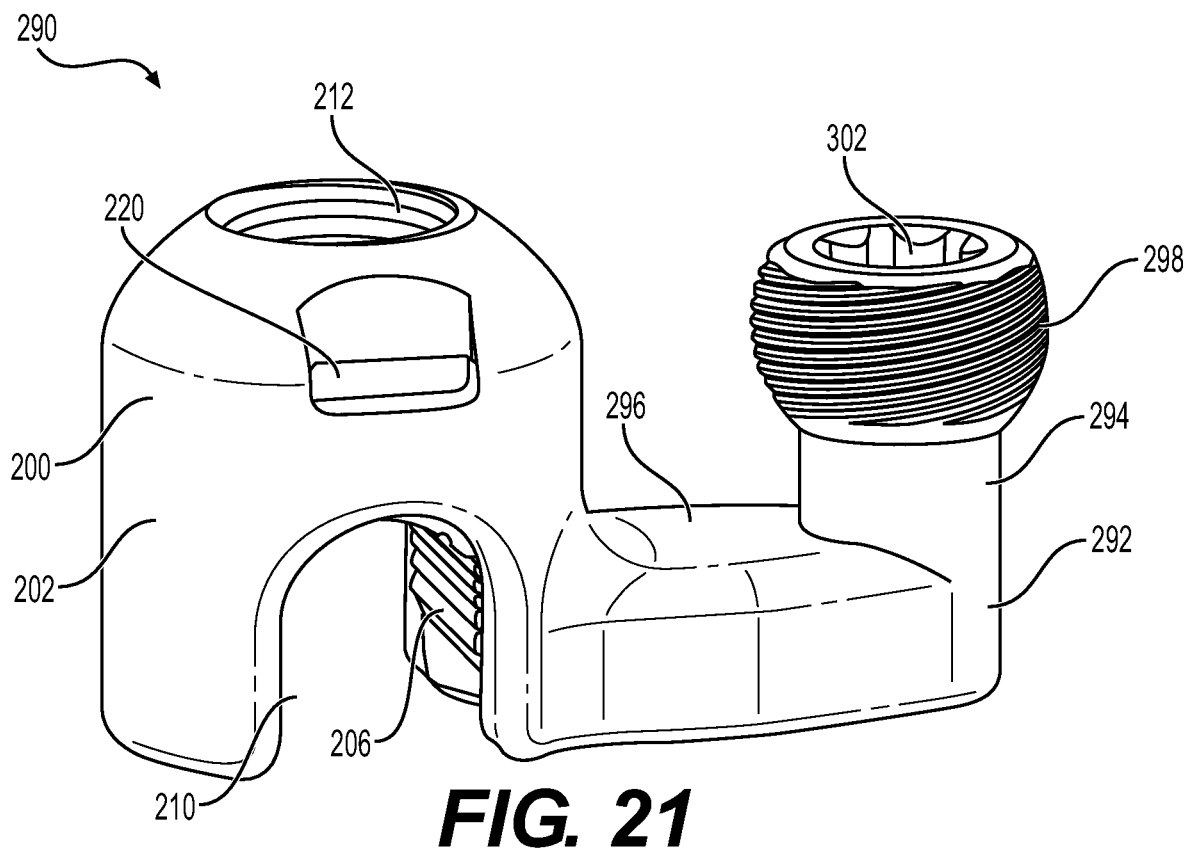
FIG. 21 shows a modular head top loading connector according to one embodiment.
Figure 22A:
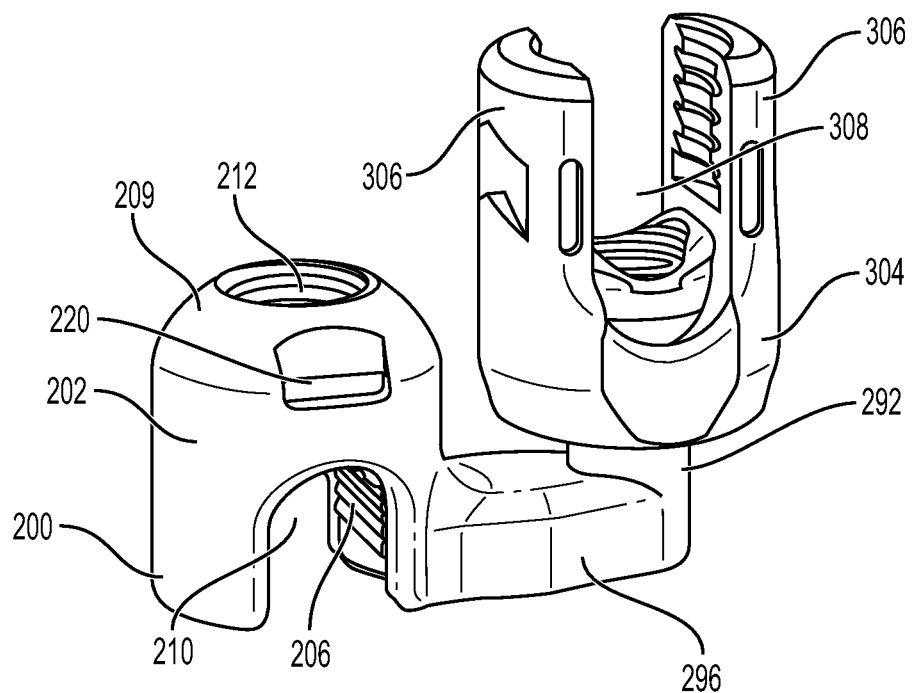
FIGS. 22A-22B show the modular head top loading connector of FIG. 21 with a modular tulip-style screw head and a headed rod, respectively.
Figure 22B:
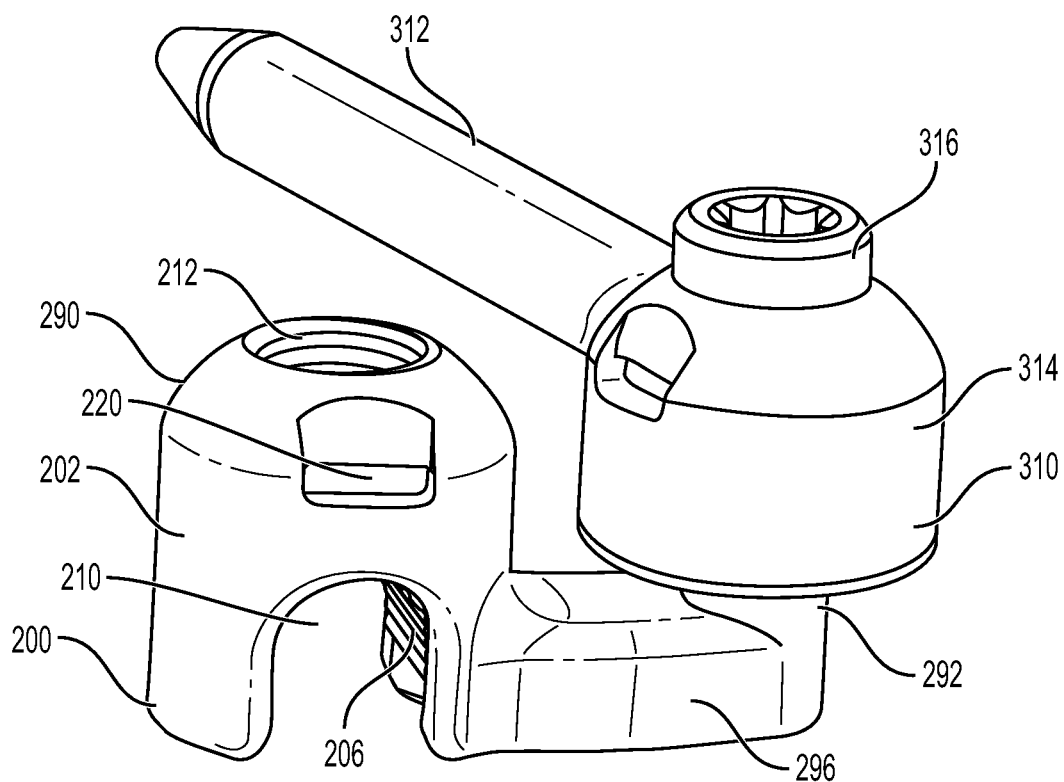

Turning now to FIGS. 21 and 22A-22B, a modular head top loading connector or implant 290 is shown according to one embodiment. The modular head top loading connector 290 includes the top loading connector portion 200 in parallel with a modular connection point 292. The modular connection point 292 allows for attachment of a modular screw head assembly 304 or a headed rod 310 (shown in FIGS. 22A and 22B, respectively).

The modular portion 292 may be in the form of a post 294 extending from a bridge 296. The bridge 296 may connect the post 294 to the top loading connector portion 200. The post 294 may extend generally orthogonally or perpendicularly from the bridge 296. It is also envisioned that the post 294 may extend at any other suitable angle or direction. The post 294 may have a partially spherical head 298 with a generally flat top surface, for example. The top of the spherical head 298 may having an instrument recess 302 configured to be engaged by an instrument. The outer surface of the spherical head 298 may be threaded or a have a roughened surface, for example, to enhance engagement with the corresponding opening in the headed rod 310 or tulip assembly 304.

As best seen in FIG. 22A, the modular post 294 of connector 292 may be configured to receive a tulip assembly 304. The tulip 304 may be configured to receive a second rod. The tulip 304 may include opposed arms 306 defining a passage 308 therebetween. The passage or rod slot 308 may comprise a generally U-shaped passage or through-opening. Inner surfaces of the arms 306 may include a threaded portion configured to engage with a threaded locking cap. The tulip 304 is configured to rotate or articulate about the spherical head 298 such that the second rod may be aligned substantially parallel, angled, or axially offset relative to the rod secured in the top loading connector portion 200. Once the desired orientation of the second rod relative to the first rod is achieved, a threaded locking cap may be positioned to secure the rod in the tulip 304 and secure the position of the tulip 304 relative to the connector 290.

As best seen in FIG. 22B, the modular post 294 of the connector 292 may be configured to receive a headed rod 310. The headed rod 310 includes a rod portion 312 with modular connection point 314 at a first end and terminating at a second free end. Connection point 314 has an opening sized and dimensioned to receive the spherical head 298 and one or more clamping elements positioned in the connection point 314 are configured to retain the spherical head 298 therein. For example, the headed rod 310 may include one or more of the connectors described in U.S. Pat. No. 10,874,440, which is incorporated by reference herein in its entirety for all purposes. The connection point 314 may include a threaded connector, such as, for example, a fastener or set screw 316 rotatably connected to the headed rod 310 to secure headed rod 310 to connector 290. The headed rod 310 is configured to rotate or articulate about the spherical head 298 such that the integrated rod 310 may be aligned substantially parallel, angled, or axially offset relative to the first rod in the top loading connector portion 200. Once the desired orientation of the integrated rod 310 relative to the first rod is achieved, the set screw 316 may be tightened to secure headed rod 310 to the connector 290 and secure the relative position of the headed rod 310 relative to the connector 290.

The top loading connector portion 200 offer surgeons the ability to attach instrumentation to existing spinal rod constructs from above. Attaching directly to existing instrumentation may save operating time, cause less disruption to the patient, and minimize patient recovery time. Bone growth around the existing spinal rod may make attaching connectors difficult. The surgeon may need to remove a portion of this bone growth around the rod in order to attach spinal rod connectors. Since this bone growth may be important for spinal stability and relief of patient symptoms, top loading connector portions 200 may require minimal space around the rod or connect to an area of the rod where bone removal is less challenging. Patient positioning during revision surgeries makes removing bone growth on the top of the rod less challenging than the sides or underneath of the existing rod. Therefore, top loading connectors 260, 270, 280, 290 may be useful during revision surgeries when there is a need to extend fixation to adjacent spinal levels.

In some embodiments, differences in screw trajectory and location between the existing construct and the new screws may make connecting two segments difficult. In some instances, it may be desirable for connector implants to be able to pivot or rotate in order to accommodate these differences. The spinal connector implants may be able to pivot or rotate in order to ease the connection between existing constructs and adjacent level(s) in revision surgeries.

Figure 23:
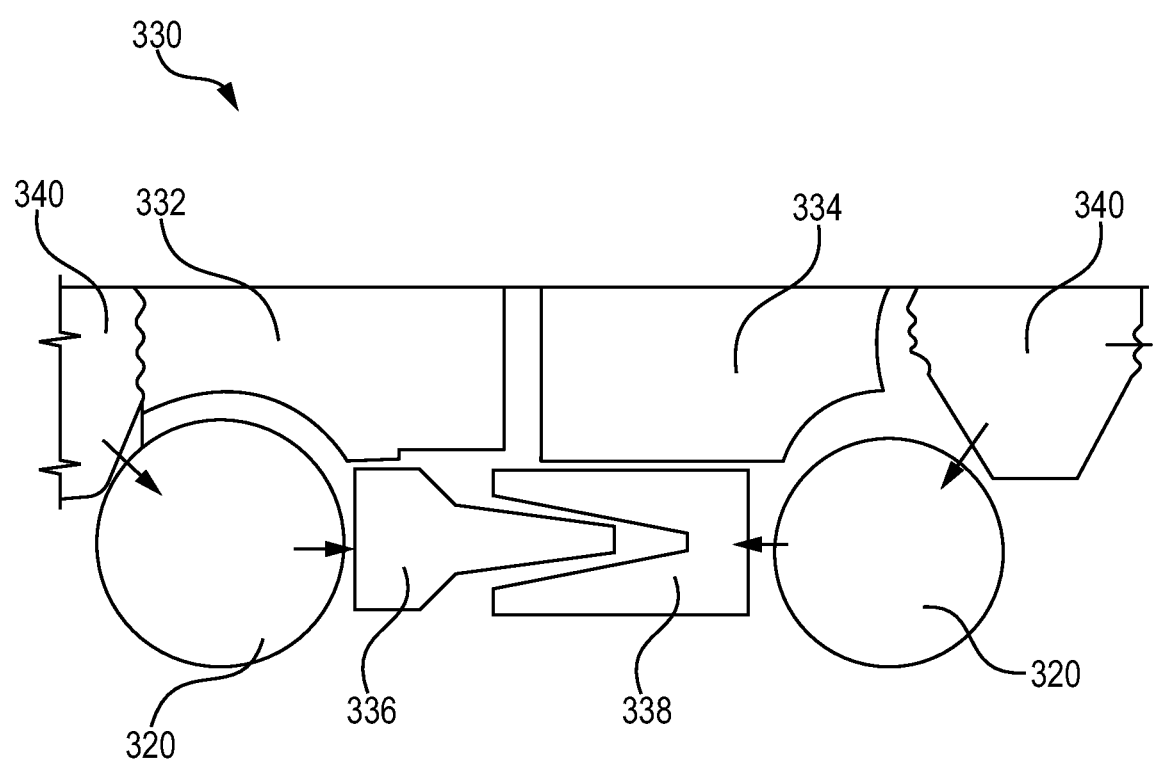
FIG. 23 shows a pivoting connector for coupling two rods according to one embodiment.

Turning now to FIG. 23, a pivoting connector or implant 330 according to one embodiment is shown. The connector 330 may allow for the connection of two parallel rods 320 also allowing for some co-planar misalignment. The connector 330 may include a first connector side or portion 332 and a second connector side or portion 334. The first connector portion 332 may be attached to a conical taper 336 and the second connector portion 334 may be attached to a conical recess 338 sized and configured to matingly receive the conical taper 336. The first and second connector portions 332, 334 are configured to rotate about the mating conical interface 336, 338. First and second locking members or threaded set screws 340 may be provided to secure the rods 320 and lock the relative position of the first and second connector portions 332, 334. When the rods 320 are locked with the set screws 340, the rods 320 push against the mating tapered portions 336, 338 to push them together, thereby clamping and locking the conical interface 336, 338.

Figure 24A:
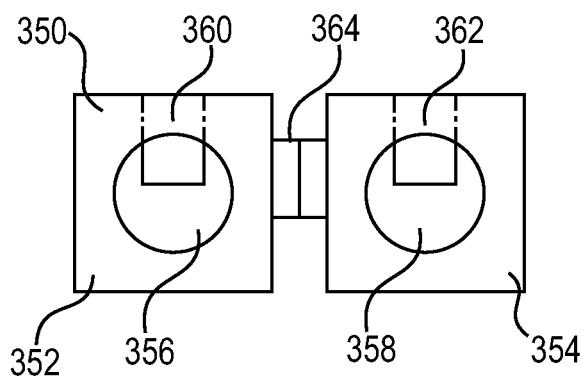
FIGS. 24A-24D depict examples of pivoting connectors using a stargrind interface.
Figure 24B:
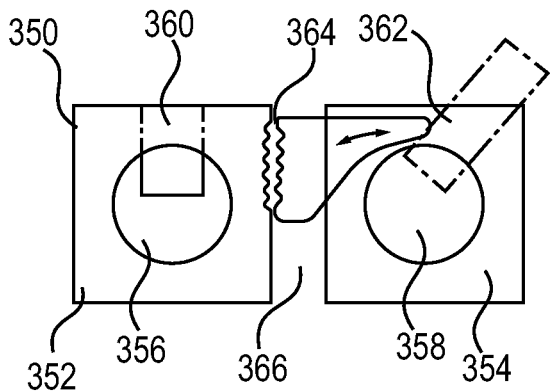
Figure 24C:
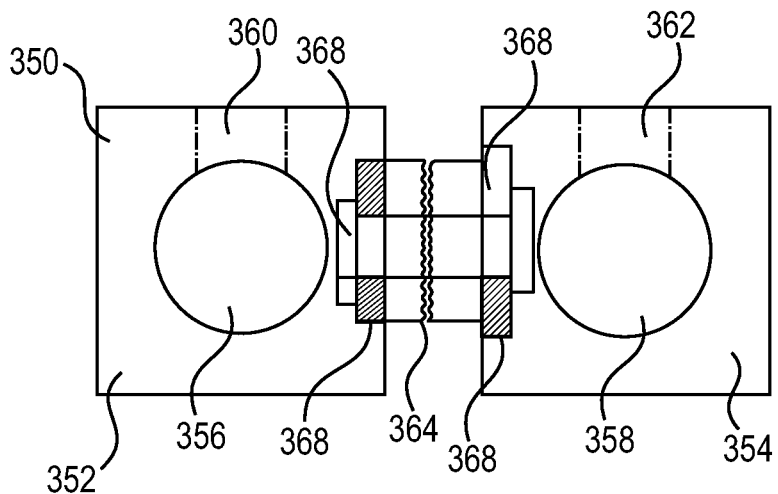

Turning now to FIGS. 24A-24D, examples of pivoting connectors or implants 350 with stargrind interfaces 364 for coupling two rods are shown. In FIGS. 24A-24C, the connectors 350 include a first connector side, portion, or block 352 and a second connector side, portion, or block 354. The first connector portion 352 may define a first rod slot 356 and the second connector portion 354 may define a second rod slot 358. One or both of the first and second rod slots 356, 358 may be closed slots for fully encircling the rods. Alternatively, one or both of the first and second rod sots 356, 358 may be open slots, for example, with a c-shaped recess configured for side-loading. The first connector portion 352 has a first hole 360 in fluid communication with the first rod slot 356 and the second connector portion 354 has a second hole 362 in fluid communication with the second rod slot 358. The holes 360, 362 may be perpendicular or angled to the respective rod slots 356, 358. The first and second holes 360, 362 may include a threaded portion configured to interface with threaded locking members or set screws able to travel up and down within the respective threaded holes 360, 362. When in a downward position, a bottom surface of the locking member or set screw is configured to contact and secure the spinal rod within the connector portions 352, 354 of the implant 350.

Figure 24D:
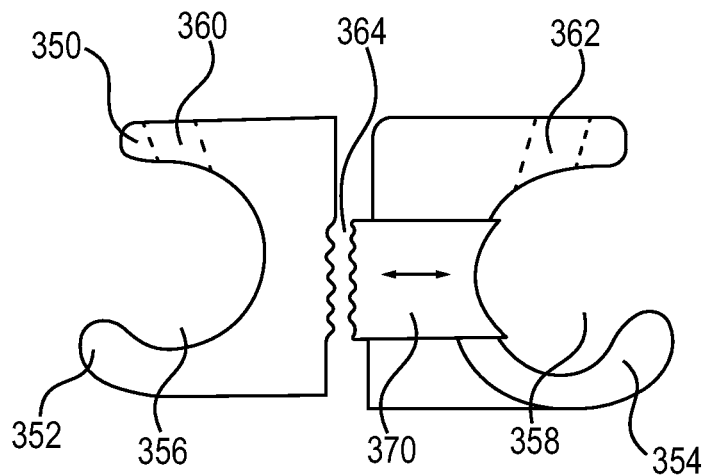

In FIG. 24A, the two connector portions 352, 354 may be pinned together to allow rotation. A stargrind interface 364 may be configured to lock the relative position of the connector portions 352, 354 into the desired orientation. In FIG. 24B, a sliding stargrind member 366 may be moveable between the connector portions 352, 354 to translate the stargrind interface 364 into engagement. In particular, the sliding stargrind member 366 may be pushed outward via a set screw in opening 362 to engage and lock the mating stargrind 364. In FIG. 24C, one or more pins may be used to connect the two connector portions 352, 354. One or more solid washers 368 may be configured to keep the stargrind 364 engaged. The washers 368 may include, for example, coned-disc spring, conical spring washers, disc springs, or Belleville type washers. A tool may be used to slide the connector portions 352, 354 apart and rotate one side to the desired angle. FIG. 24D shows an embodiment with open side-loading connector portions 352, 354. The spinal rod in connector portion 354 pushes a slider piece 370 into the first connector portion 352 to lock the connectors together. The slider 370 may be pushed via the spinal rod when a set screw is threaded downwardly in opening 362 and into contact with the spinal rod.

Figure 25A:
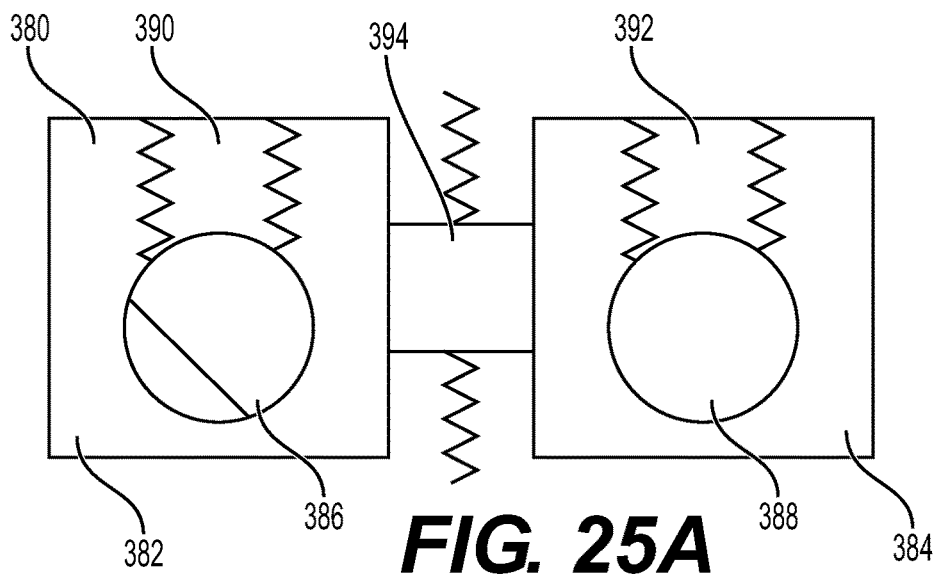
FIGS. 25A-25C show a pivoting connector with a rotating pin according to one embodiment.
Figure 25B:
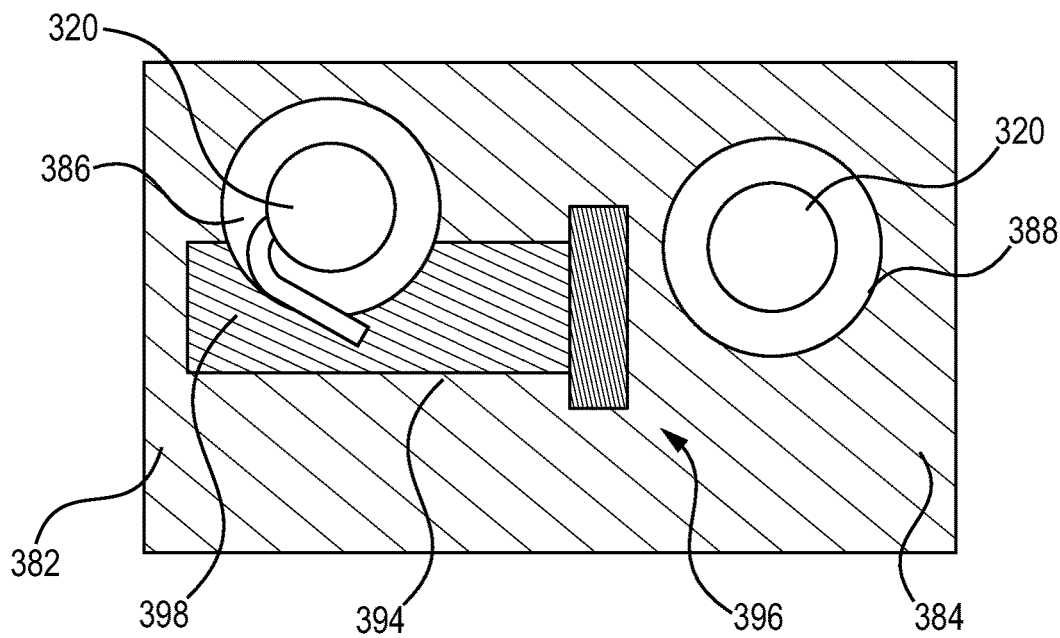
Figure 25C:
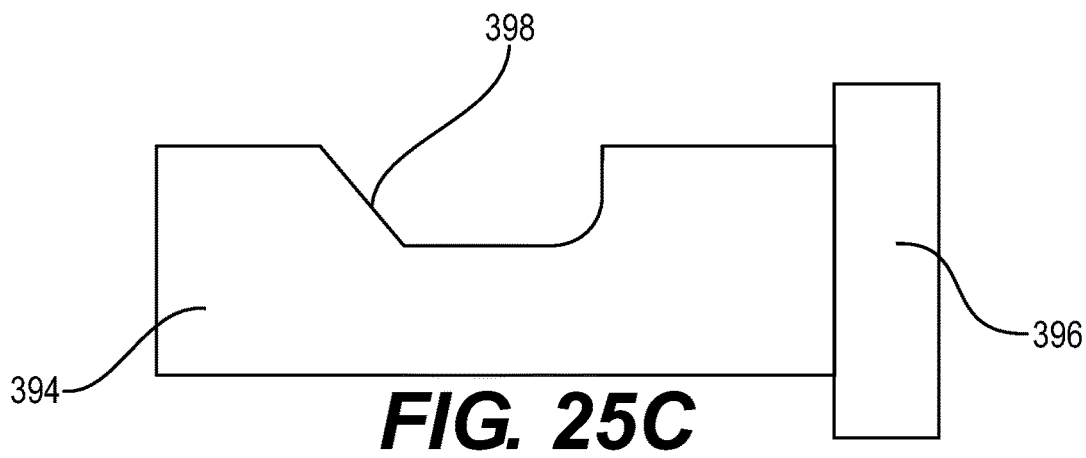

Turning now to FIGS. 25A-25C, a pivoting connector or implant 380 with a rotating pin 394 for coupling two rods 320 is shown. Similar to connector 350, connector 380 includes a first connector portion or first block 382 and a second connector portion or second block 384. The first and second portions 382, 384 include closed rod slots 386, 388 with intersecting locking member holes 390, 392. The surfaces between the blocks 382, 384 may optionally include a stargrind, grit blast, or other frictioned surface to help hold positioning. A rotating pin 394 couples the two blocks 382 together. The rotating pin 394 may include a base 396 anchored in one of the blocks 382, 384 and a free end extending into the other block 382, 384. A ramp 398 on the pin 394 may rotate into alignment with the rod slot 386, 388. When a locking member or set screw is threaded downwardly through the locking member hole 390, 392 and into engagement with the spinal rod 320, the spinal rod 320 pushes down and against the ramp 398, thereby pulling the blocks 382, 384 toward one another. This secures the relative positions of the blocks 382, 384.

Figure 26A:
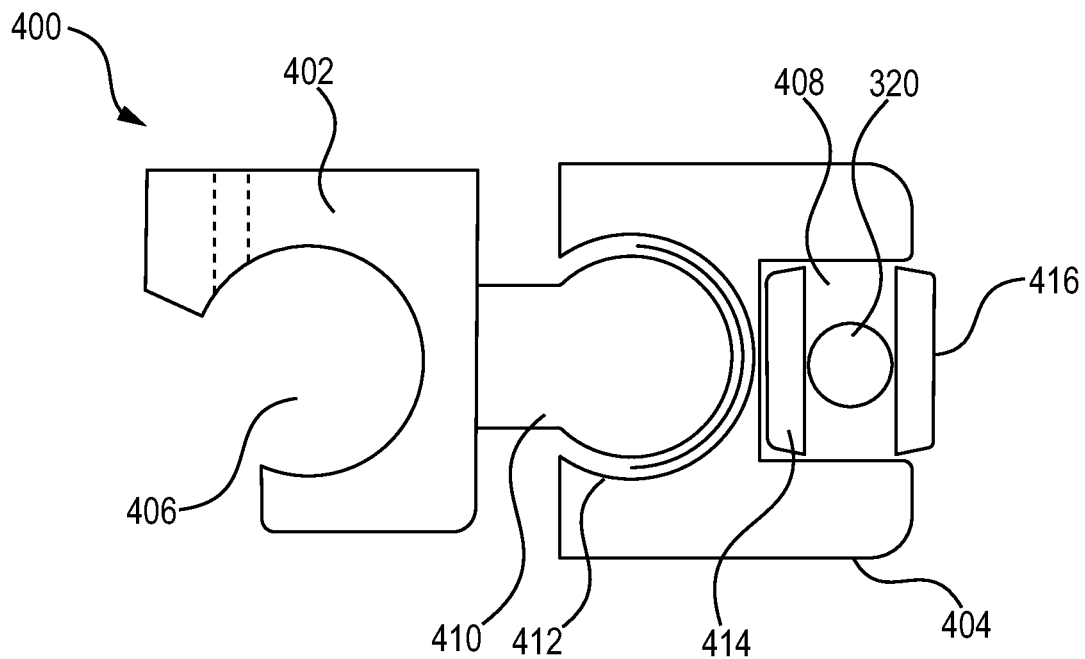
FIGS. 26A-26B show a pivoting connector with a post according to one embodiment.
Figure 26B:
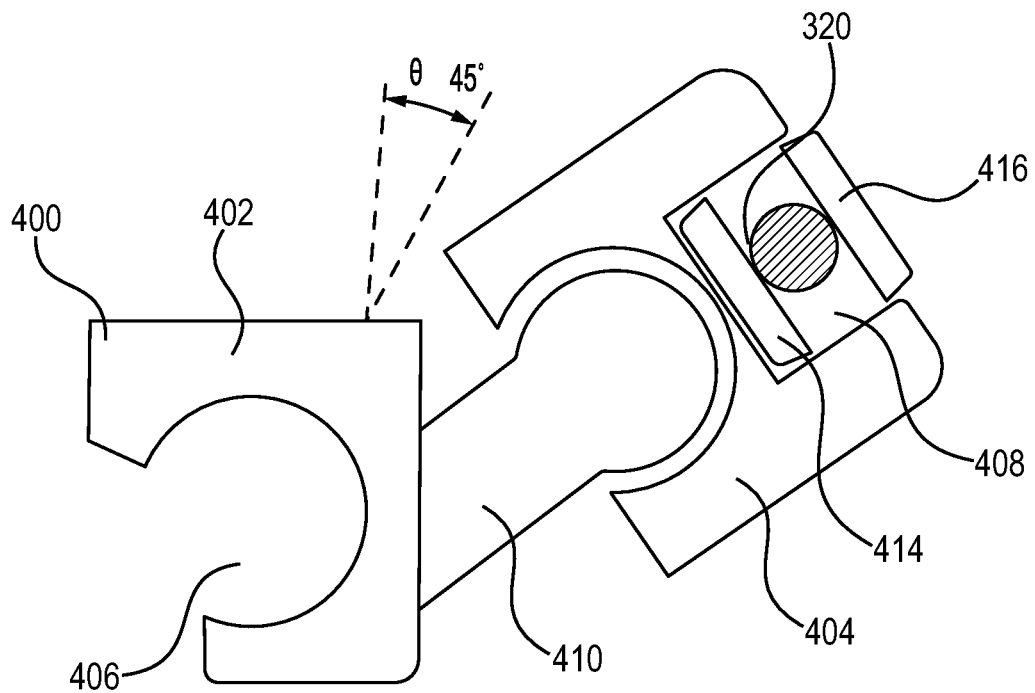

Turning now to FIGS. 26A-26B, a pivoting connector or implant 400 with a post 410 is shown according to one embodiment. The connector 400 includes a first portion 402 and a second portion 404 coupled and pivotable about the post 410. The first portion 402 includes an open rod slot 406 and the second portion 404 defines a tulip-style body, similar to implant 160, with a U-shaped rod slot 408. The post 410 may define a spherical head similar to modular post 294. The second portion 404 may pivot at an angle θ, for example, up to 45°, relative to the first portion 402. A clamp 412 and saddle 414 may secure the second portion 404 relative to the first portion 402. When a threaded locking cap or set screw 416 is threaded downward onto the rod 320, the rod 320 presses on the saddle 414 and clamp 412, thereby fixing the relative position of the second portion 404 relative to the first portion 402.

Figure 27A:
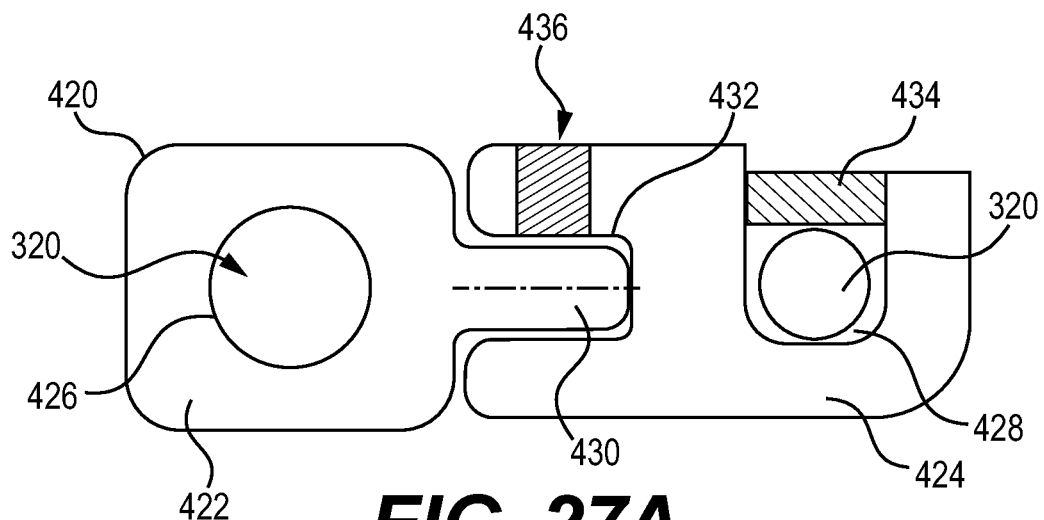
FIGS. 27A-27C depict examples of pivoting connectors with a leg joint.
Figure 27B:
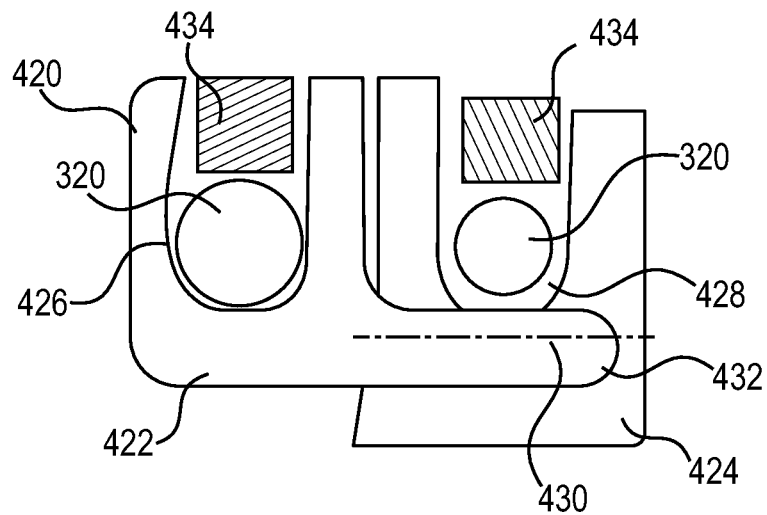
Figure 27C:
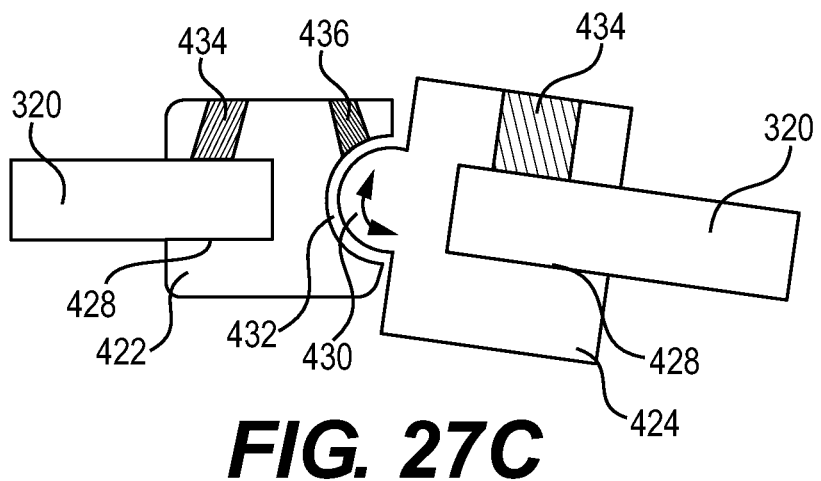

Turning now to FIGS. 27A-27C, examples of pivoting connectors or implants 420 with a leg joint 430, 432 are shown. The pivoting connectors 420 include a first connector portion 422 with a first rod slot 426 and a second connector portion 424 with a second rod slot 428. A leg 430 extends from one connector portion 422, 424 into a slot 432 in the opposite connector portion 422, 424. The leg joint 430, 432 allows the connector portions 422, 424 to rotate or pivot relative to one another, thereby allowing for adjustment of the rods 320.

In FIG. 27A, the pivoting connector 420 is a parallel connector providing for rotation of the connector portions 422, 424 about the leg 430. The first rod slot 422 in the first connector portion 422 is a closed slot for fully encircling the rod 320. The second connector portion 424 has a tulip-shaped body with a U-shaped rod slot 428. Each of the rods 320 are secured in the respective rod slots 426, 428 with a locking member or set screw 434. A separate locking member or set screw 436 is configured to engage and lock the leg 430, thereby securing the orientation of the first and second connector portions 422, 424.

In FIG. 27B, the pivoting connector 420 is another parallel connector providing for rotation of the connector portions 422, 424 about the leg 430. The first and second connector portions 422, 424 each have a tulip-shaped body with a U-shaped rod slot 426, 428. The rods 320 are secured in the slots 426, 428 by respective set screws 434. In this embodiment, the leg 430 is locked in position by the rod 320 in slot 428. The leg slot 432 intersects rod slot 428. When the set screw 434 is threaded downwardly, the set screw 434 pushes against the rod 320 which pushes against the leg 430, thereby locking the positions of the first and second connectors 422, 424.

In FIG. 27C, the pivoting connector 420 is an in-line connector providing for rotation and/or pivoting of the connector portions 422, 424. The first and second connector portions 422, 424 may have tulip-shaped or closed openings allowing for in-line positioning of the first and second rods 320. In this embodiment, the leg joint 430, 432 may be partially spherical or rounded to permit rotational and/or pivotal motion of the first and second connector portions 422, 424. The pivoting connector 420 may allow the rods 320 to be in-line and co-axial or angled with respect to one another. A separate locking member or set screw 436 is configured to engage and lock the leg 430, thereby securing the orientation of the first and second connector portions 422, 424.

Turning now to FIGS. 28A-28D, examples of rotating parallel connectors 440 with interlocking geometries are shown. The pivoting connectors 440 include a first connector portion 442 with a first rod slot 446 and a second connector portion 444 with a second rod slot 448. A shaft 450 extends from one connector portion 442, 444 into a slot 452 in the opposite connector portion 442, 444. The shaft joint 450, 452 allows the connector portions 442, 444 to rotate or pivot relative to one another, thereby allowing for adjustment of the rods 320.

Figure 28A:
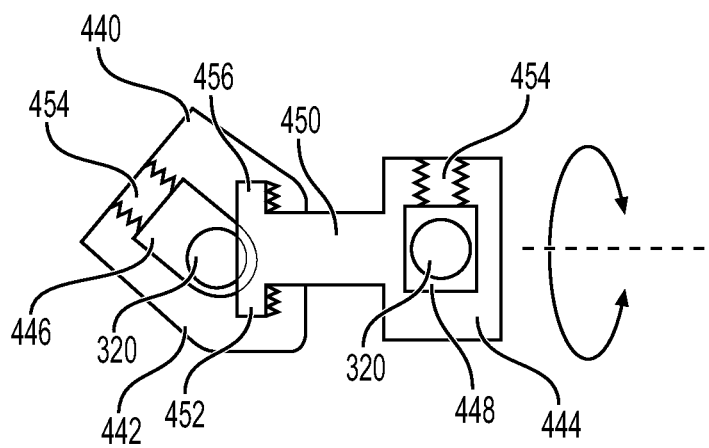
FIGS. 28A-28D show examples of rotating connectors with interlocking geometries.

In FIG. 28A, the first connector portion 442 includes a tulip-shaped body with a U-shaped rod slot 446 and the second connector portion 444 has a closed-style body. Each of the rods 320 are secured in the respective slots 446, 448 by a locking member or set screw 454. The shaft 450 may be integral with one of the connector portions 442, 444. A free end of the shaft 450 may extend into the other connector portion 442, 444. In this embodiment, an enlarged free end 456 anchors the shaft 450 into the first connector portion 442. The connector portions 442, 444 are free to rotate until locked. When the set screw 454 is threaded downwardly onto rod 320 in slot 446, the rod 320 pushes against the free end 456 of the shaft 450, thereby locking the rotation of the components.

Figure 28B:
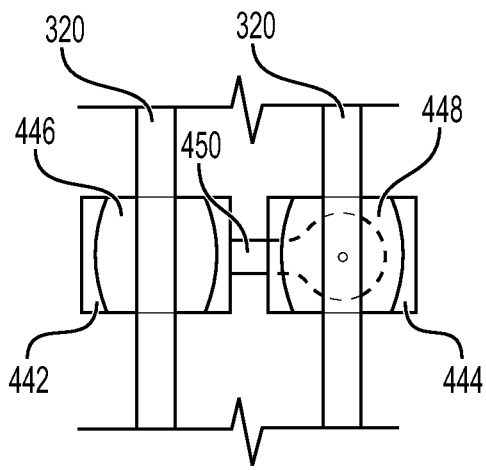
Figure 28C:
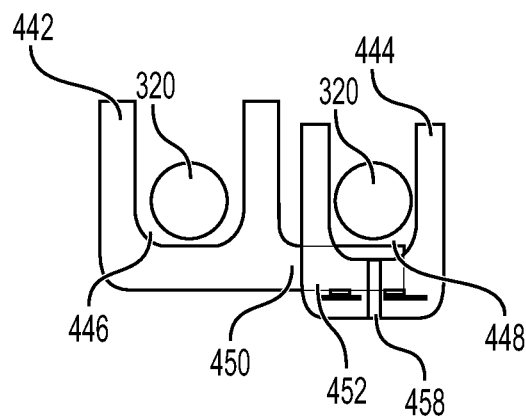

In FIGS. 28B-28C, the first and second connector portions 442, 444 may be in the form of tulips. The shaft 450 may be integral with one of the tulips and extend into a mating slot 452 on the opposite tulip. Each of the rods 320 are secured in the respective slots 446, 448 by a locking member or set screw 454. In this embodiment, the shaft 450 may be pinned 458 to prevent translation. When a downward force from the set screw 454 is applied to the rod 320 in rod slot 448, the rod 320 presses against the shaft 450 and locks movement of the connector portions 442, 444.

Figure 28D:
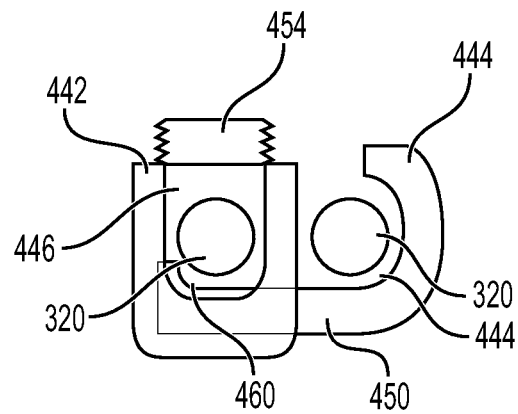

In FIG. 28D, the first connector portion 442 may be a tulip and the second connector portion 444 may have a L-shaped body. The shaft 450 may be an integral section of the L-shaped body of the second connector portion 444. In this embodiment, the shaft 450 may include a ramped slot or surface 460. As the set screw 545 is tightened against rod 320 in slot 446, the rod 320 is clamped against the ramped slot 460, thereby locking the positions of the connector portions 442, 444.

Turning now to FIGS. 29A-29D, a pivoting connector or implant 470 according to one embodiment is shown. The pivoting connector 470 includes a first connector portion 472 with a first rod slot 476 and a second connector portion 474 with a second rod slot 447. A T-jack 480 extends from one connector portion 472, 474 into a slot 482 in the opposite connector portion 472, 474. The T-jack 480 allows the connector portions 472, 474 to rotate or pivot relative to one another, thereby allowing for adjustment of the rods 320.

The first and second connector portions 472, 474 may define closed slots 476, 478 for fully encircling the respective rods 320. The mating inner facing surfaces of the first and second connector portions 472, 474 may be rounded or domed to form a ball joint, thereby allowing for pivotal and/or rotational movement. The T-jack 480 may include an elongate body with a transverse cross member 484. The cross member 484 may terminate at a free end 486. The free end 486 may be received in the slot 482 in the first connector portion 472 and the elongate body of the T-jack 480 may be received in the second connector portion 474. The free end 486 of the T-jack 480 may be rounded or spherical to provide pivotable movement between the components. The free end 486 may be loose in the slot 482 to allow movement before locking. A cam 488 may be configured to push the T-jack 480 backward, thereby pulling together and locking the first and second connector portions 472, 474.

Turning now to FIG. 30, a connector portion or housing 490 configured to accept a range of rod diameters is shown according to one embodiment. The connector portion 490 may be a top loading connector that attaches onto one spinal rod 320 from above and a second connector portion (not shown) may attach onto the other spinal rod in any of the configurations shown herein. The connector portion 490 may have a hollow housing with inner ramped surfaces 492 configured to engage with a clamp 494. The clamp 494 may be split into two portions and configured to enclose the rod 320. A locking member or set screw 496 may be threaded downwardly onto the clamp 494, which slides against the ramps 492 to tighten the clamp 494 around the rod 320. The clamp 494 can accept a range of rod diameters.

The locking screw 496 may have a thru hole to allow a shaft 498 of a driver instrument 500 therethrough. The cannulated driver 500 may have a spring-loaded shaft 498 to provide feedback based on axial translation of the shaft 498. The shaft 498 may pass through the locking screw 496 and into contact with the rod 320. With the feedback from the instrument 500, the user can determine whether the rod 320 is in place. The semi-flexible clamp 494 may be closed via the locking screw 496 and ramped surfaces 492 on the housing body.

Turning now to FIG. 31, a connector portion or housing 510 configured to accept a range of rod diameters is shown according to one embodiment. The connector portion 510 may be a top loading connector that attaches onto one spinal rod 320 from above and a second connector portion (not shown) may attach onto the other spinal rod in any of the configurations shown herein. The connector portion 510 may retain a fork-like structure 512 attached to a set screw 514. The rod 320 snaps into the fork 512. When the set screw 514 is locked downward, the fork 512 clamps around the rod 320, thereby locking the rod 320 in the connector 510.

With reference to FIG. 32, a connector portion or housing 520 configured to accept a range of rod diameters is shown according to one embodiment. The connector portion 520 may be a top loading connector that attaches onto one spinal rod 320 from above and a second connector portion (not shown) may attach onto the other spinal rod in any of the configurations shown herein. The connector portion 520 may retain a pair of prong arms 522 attached to a set screw 524. The prongs 522 may be forced apart via a spring 526. The set screw 524 may include i-slots with end stops to accept the ends of the prongs 522. When the set screw 524 is in the open position, the spring distance is maintained to allow the capture prongs 522 to snap over the rod 320. Advancing the set screw 524 brings the angled prong arms 522 together, thereby securing the rod 320 in the housing 520.

Figure 33A:
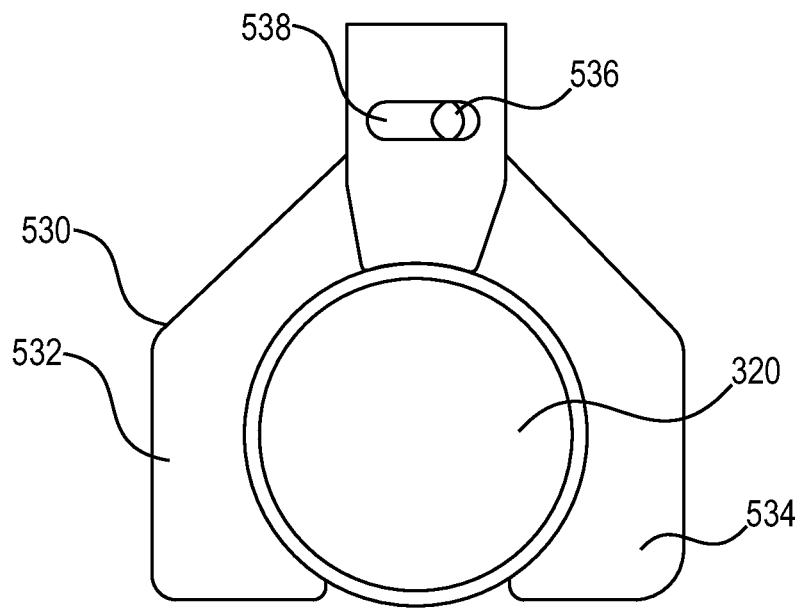
FIGS. 33A-33B show a nesting connector portion configured to accept multiple rod sizes according to one embodiment.
Figure 33B:
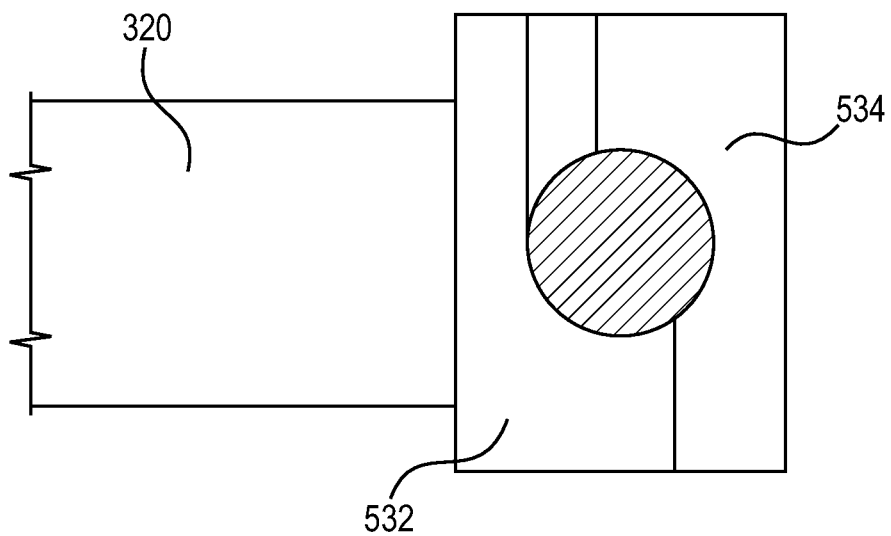

Turning now to FIGS. 33A-33B, a connector portion or housing 530 configured to accept a range of rod diameters is shown according to one embodiment. The connector portion 530 may be a top loading connector that attaches onto one spinal rod 320 from above and a second connector portion (not shown) may attach onto the other spinal rod in any of the configurations shown herein. The connector portion 530 may include a first half or first arm 532 and a second half or second arm 534 nested together to capture the rod 320 therebetween. A pin 536 and slot 538 may be configured to allow translation of the arms 532, 534. The arms 532, 534 may translate toward and away from one another to accept and secure rods 320 of varying diameters.

Figure 34A:
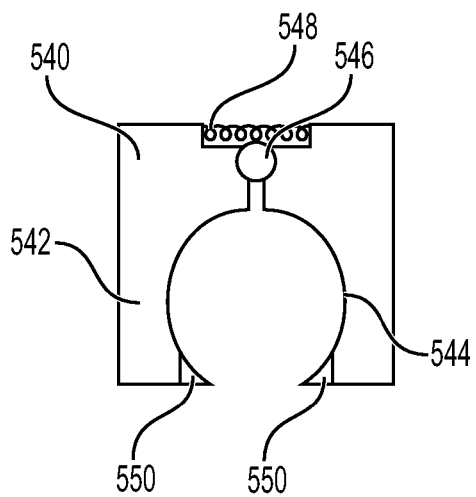
FIGS. 34A-34C show a connector portion with a pair of pinchers for securing a rod according to one embodiment.
Figure 34B:
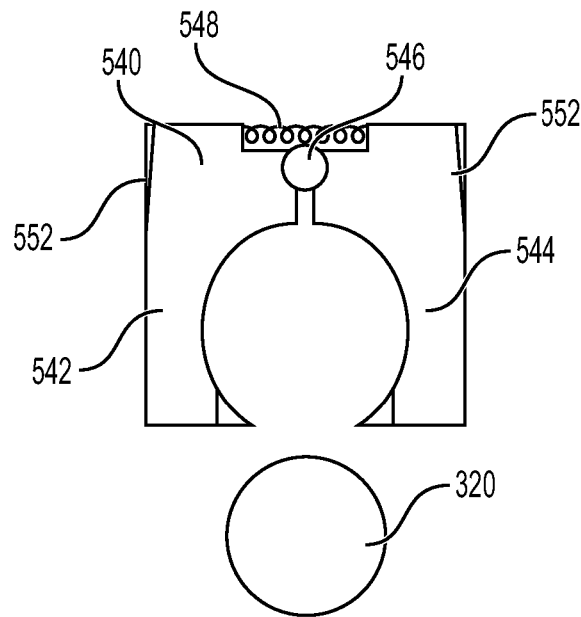
Figure 34C:
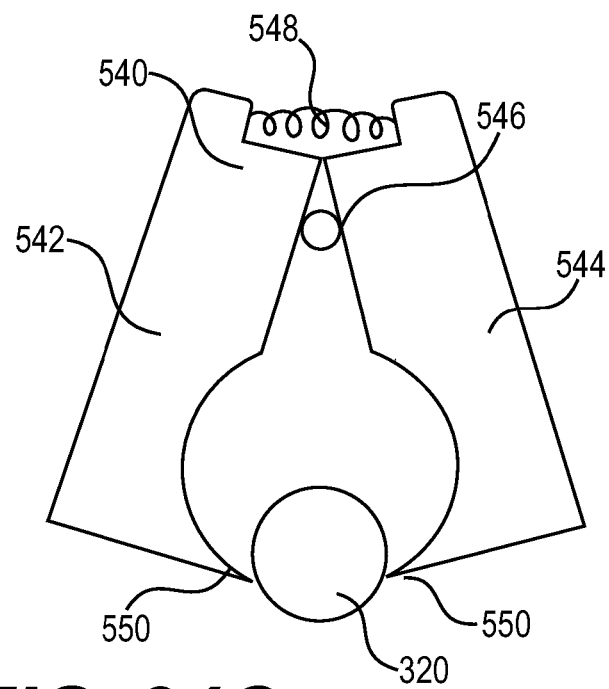

Turning now to FIGS. 34A-34C, a connector portion 540 for securing a rod 320 is shown according to one embodiment. The connector portion 54 may include a pair of pinchers 542, 544 pivotable about a pin 546. A spring 548 at the top of the connector portion 540 may provide tension to open the pinchers 542, 544 to receive the rod 320 therebetween. The tips 550 of the pinchers 542, 544 may be pointed or sharpened to grasp or retain the rod 320. One or more upper side surfaces of the pinchers 542, 544 may be beveled or chamfered to act as an engagement point with an outer lock (not shown). When received in the outer lock, the pinchers 542, 544 may squeeze together to secure the rod 320.

Figure 35A:
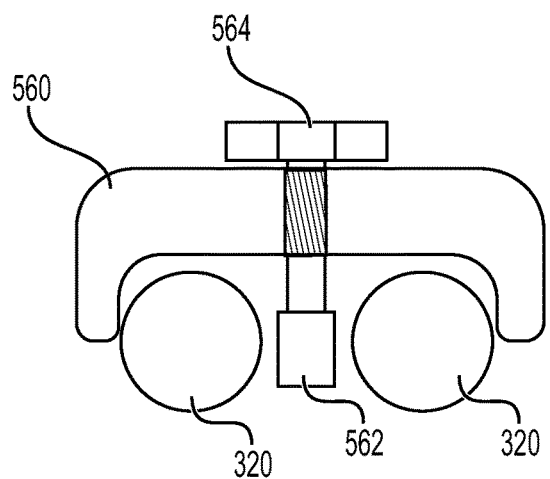
FIGS. 35A-35C show a parallel connector with a rotating wedge according to one embodiment.
Figure 35B:
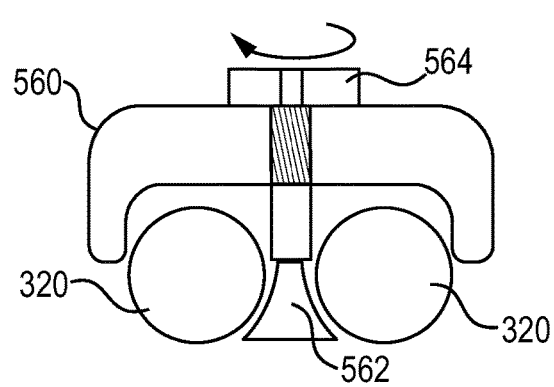
Figure 35C:
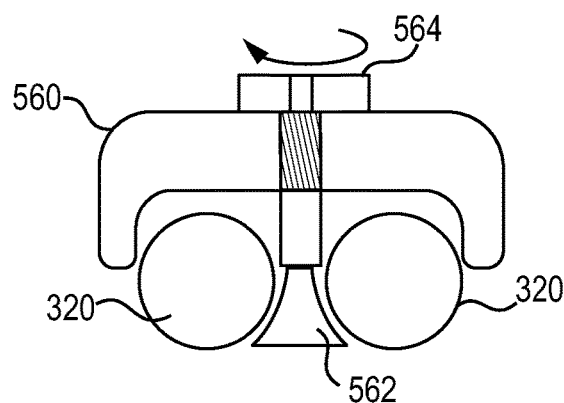

Turning now to FIGS. 35A-35C, a parallel connector or implant 560 is shown according to one embodiment. The connector 560 includes a body configured to cradle two parallel rods 320. The ends of the connector 560 may overhang with rounded or tapered surfaces to capture the rods 320. A rotating cam or wedge 562 is positioned between the two rods 320. As shown in FIG. 35A, the rotating wedge 562 is disengaged from the rods 320 and rods 320 of any diameter may be positioned within the connector 560. In FIG. 35B, a screw or nut 564 on the connector 560 is rotated to rotate the cam or wedge 562, thereby engaging the rods 320 in the connector 560. In FIG. 35C, the wedge 562 is in a final locking position, fully securing the rods 320 to the connector 560.

Turning now to FIG. 36, a parallel connector or implant 570 is shown according to one embodiment. Similar to implant 560, implant 570 is configured to cradle two parallel rods 320. In this embodiment, the connector 570 itself acts as a clamp with a first moveable clamp portion 572 and a second moveable clamp portion 574 connected and pivotable about a pin 576. A static wedge 578 may be positioned between the two rods 320. When a nut 580 is rotated, the moveable clamp portions 572, 574 pinches together, thereby closing the clamp and securing the rods 320 therein.

Turning now to FIGS. 37A-37B, a parallel connector or implant 590 is shown according to one embodiment. Similar to implant 560, implant 590 includes a rotating cam 592 configured to secure the rods 320 in the implant 590. The connector 590 includes a body with an overhang at one end having rounded or tapered surfaces to capture one of the rods 320. The cam 592 is positioned at the opposite end of the connector 590 to position the two rods 320 therebetween. A slidable wedge 596 may be positioned between the two rods 320. The slidable wedge 596 may slide or translate between the rods 320. When a nut 594 is rotated, the cam 592 may be locked against the rod 320. Rotating the nut 594 turns the cam 592 and compresses both rods 320 against the slidable wedge 596 and between the overhang of the connector 590 and the cam 592, thereby securing the rods 320.

Figure 38:
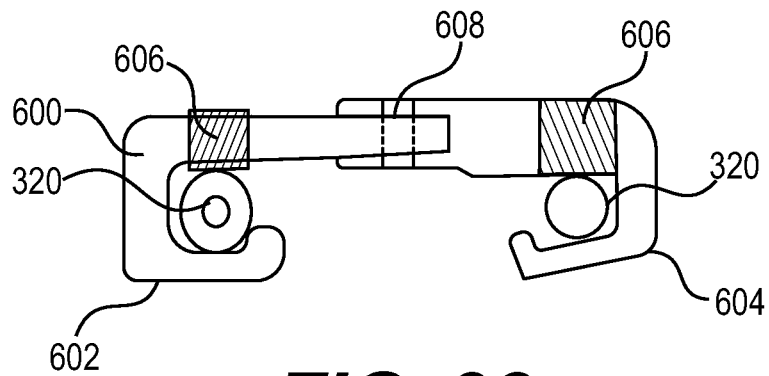
FIG. 38 shows a telescoping connector according to one embodiment.

Turning now to FIG. 38, a telescoping parallel connector or implant 600 is shown according to one embodiment. The telescoping connector 600 includes a first portion 602 with a hook for retaining a first rod 320 and a second portion 604 with a hook for retaining a second rod 320. A locking member or set screw 606 may be provided to secure each of the rods 320. The hook portions 602, 604 are able to telescope toward and away from one another. The relative positions of the rods 320 may be locked by a locking member 608 connecting the two hook portions 602, 604.

Figure 39A:
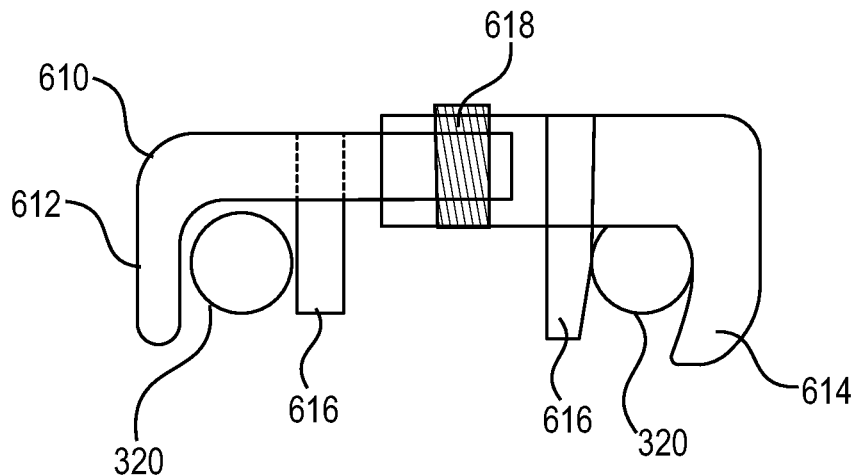
FIGS. 39A-39B shows an example of a telescoping connector with rotating cams according to one embodiment.
Figure 39B:
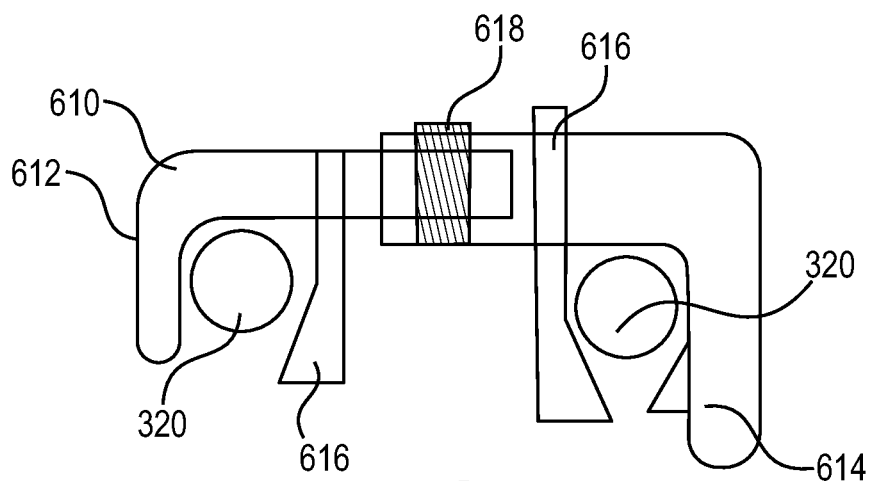

Turning now to FIGS. 39A-39B, a telescoping parallel connector or implant 610 is shown according to one embodiment. Similar to implant 600, implant 610 telescopes to vary the distance between two rods 320. In this embodiment, two cam-style locks 616 are configured to retain the rods 320. The first rod 320 is secured in the first portion 612 between an overhang and a first cam lock 616 and the second rod 320 is secured in the second portion 614 between an overhang and a second cam lock 616. FIG. 39A shows the cams 616 in the unlocked position and FIG. 39B shows the cams 616 in the locked position. After telescoping to the desired distance, the relative positions of the rods 320 may be locked by a locking member 618.

Turning now to FIG. 40, a top loading connector portion 620 configured to accept a range of rod diameters is shown according to one embodiment. The connector portion 620 may be a top loading connector that attaches onto one spinal rod 320 from above and a second connector portion (not shown) may attach onto the other spinal rod in any of the configurations shown herein. The connector portion 620 defines a rod slot 622 at the bottom of the body. The rod 320 may snap in place to fit in the rod slot 622. A clearance cut 624 in fluid communication with the rod slot 622 allows for flexing of the body. A locking ring 626 is configured to secure the rod 320 in the rod slot 622. The locking ring 626 squeezes as the ring 626 travels down the body of the connector 620, thereby securing the rod 320.

Turning now to FIGS. 41A-41B, a parallel connector or implant 630 with sliding blockers 634 is shown according to one embodiment. The connector 630 defines a pair of rod slots 632 each configured to receive a rod 320. A blocker 634 configured to slide or translate into contact with the rod 320 locks the rod 320 in position. As shown, a pair of sliding blockers 634 may secure each of the respective rods 320 in the rod slots 632. The sliding blockers 634 may be spring loaded with spring 636. A set screw 638 with a ramp or cone on the end may be configured to force the sliding blockers 634 into place, thereby securing the rods 320.

The rotating and pivoting connectors may improve the ease of surgeons in attaching instrumentation to existing spinal rod constructs. Spinal connector implants that offer the ability to rotate and/or pivot may save operating time, cause less disruption to the patient, and may minimize patient recovery time. Static connectors may require the surgeon to bend the rod into a specific shape to extend fixation. Connector implants that rotate and/or pivot may allow for more options for the surgeon to place the rod especially during a revision surgery.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A connector implant comprising:
 a connector body having an upper surface, a lower surface, a front, a back, and two opposed side surfaces, the connector body having a first clamping portion and a second clamping portion, the first clamping portion having a first passage sized and dimensioned to receive a first rod, and the second clamping portion having a second passage sized and dimensioned to receive a second rod, the connector body having an engagement recess defined with the side surface, wherein the engagement recess is a T-shaped indentation configured to interface with an implant inserter to help orient and manipulate the connector body into position, the first and second clamping portions respectively having a first threaded opening and a second threaded opening;
 a first locking member configured to be threaded into the first threaded opening to secure the first rod in the connector body, wherein the first locking member comprises a flange extending from a bottom surface and having a larger diameter than a diameter of the first threaded opening to keep the first locking member assembled to the connector body; and
 a second locking member configured to be threaded into the second threaded opening to secure the second rod in the connector body, wherein the second locking member comprises a conical bottom and a flange extending laterally from an upper part of the conical bottom and having a larger diameter than a diameter of the second threaded opening to keep the second locking member assembled to the connector body, wherein the first clamping portion is closed and the second clamping portion is recessed into the front of the connector body and open towards the front of the connector body.

2. The connector implant of claim 1, wherein the connector body includes two opposed engagement recesses defined within the side surfaces near the upper surface of the implant.

3. The connector implant of claim 1, wherein the T-shaped indentation includes a first recessed portion extending along the side surface from the front to the back of the connector body.

4. The connector implant of claim 3, wherein the T-shaped indentation includes a second recessed portion extending from the middle of the first recessed portion downward towards the lower surface of the connector body.

5. The connector implant of claim 4, wherein the second recessed portion includes a vertical bar having a length greater than its width.

6. The connector implant of claim 3, wherein the first recessed portion includes a horizontal bar having a length greater than its width.

7. The connector implant of claim 1, wherein the T-shaped indentation is positioned at a mid-line between the first and second clamping portions.

8. The connector implant of claim 1, wherein the first and second passages are aligned in parallel.

9. The connector implant of claim 1, wherein the first or second passage has a dual diameter to allow for the respective first or second rod to be captured in three-point contact with the connector body.

10. A connector implant comprising:
a connector body having an upper surface, a lower surface, a front, a back, and two opposed side surfaces, the connector body having a first clamping portion and a second clamping portion, the first clamping portion having a first passage sized and dimensioned to receive a first rod, and the second clamping portion having a second passage sized and dimensioned to receive a second rod, the connector body having an engagement recess defined with the side surface, wherein the engagement recess is a T-shaped indentation configured to interface with an implant inserter to help orient and manipulate the connector body into position, the first and second clamping portions respectively having a first threaded opening and a second threaded opening; and
first and second locking members configured to secure the first and second rods in the connector body, wherein the first clamping portion is closed and the second clamping portion is open and recessed into the front of the connector body, and the second locking member is configured to rotate about an axis that does not intersect with a central axis of the second rod, wherein the first and second locking members are configured to be respectively threaded into the first and second threaded openings, wherein:

the first locking member comprises a flange extending from a bottom surface and having a larger diameter than a diameter of the first threaded opening to keep the first locking member assembled to the connector body; and the second locking member comprises a conical bottom, and a flange extending laterally from an upper part of the conical bottom and having a larger diameter than a diameter of the second threaded opening to keep the second locking member assembled to the connector body.

11. The connector implant of claim 10, wherein the connector body includes two opposed engagement recesses defined within the side surfaces near the upper surface of the implant.

12. The connector implant of claim 10, wherein the T-shaped indentation includes a first recessed portion extending along the side surface from the front to the back of the connector body.

13. The connector implant of claim 12, wherein the T-shaped indentation includes a second recessed portion extending from the middle of the first recessed portion downward towards the lower surface of the connector body.

14. The connector implant of claim 13, wherein the second recessed portion includes a vertical bar having a length greater than its width.

15. The connector implant of claim 12, wherein the first recessed portion includes a horizontal bar having a length greater than its width.

16. The connector implant of claim 10, wherein the T-shaped indentation is positioned at a mid-line between the first and second clamping portions.

17. The connector implant of claim 10, wherein the first and second passages are aligned in parallel.

18. The connector implant of claim 10, wherein the first or second passage has a dual diameter to allow for the respective first or second rod to be captured in three-point contact with the connector body.

19. The connector implant of claim 10, wherein the second clamping portion is c-shaped.

* * * * *